US008883724B2

(12) United States Patent
Bequet Romero et al.

(10) Patent No.: US 8,883,724 B2
(45) Date of Patent: **\*Nov. 11, 2014**

(54) ACTIVE ANTIANGIOGENIC THERAPY

(75) Inventors: Mónica Bequet Romero, Ciudad de la Habana (CU); Boris Ernesto Acevedo Castro, Ciudad de la Habana (CU); Jorge Victor Gavilondo Cowley, Ciudad de la Habana (CU); Luis Enrique Fernández Molina, Ciudad de la Habana (CU); Omar Lopez Ocejo, Ciudad de la Habana (CU); Ricardo de la Caridad Silva Rodriguez, Ciudad de la Habana (CU); Alexis Musachio Lasa, Mariel (CU); Ernesto Galban Rodriguez, Ciudad de la Habana (CU); Dania Marcia Vásquez Blomquist, Ciudad de la Habana (CU)

(73) Assignee: Centro de Ingenieria Genética y Biotecnologia, Ciudad de la Habana (CU)

( * ) Notice: Subject to any disclaimer, the term of this patent is extended or adjusted under 35 U.S.C. 154(b) by 818 days.

This patent is subject to a terminal disclaimer.

(21) Appl. No.: 12/612,455

(22) Filed: Nov. 4, 2009

(65) Prior Publication Data

US 2010/0047265 A1    Feb. 25, 2010

Related U.S. Application Data

(62) Division of application No. 11/787,522, filed on Apr. 17, 2007, now abandoned, which is a division of application No. 10/511,384, filed as application No. PCT/CU03/00004 on Apr. 11, 2003, now Pat. No. 7,556,809.

(30) Foreign Application Priority Data

Apr. 15, 2002    (CU) .......................................... 76/02

(51) Int. Cl.
| | |
|---|---|
| *A61K 38/18* | (2006.01) |
| *A61K 39/395* | (2006.01) |
| *C07K 14/475* | (2006.01) |
| *C07K 16/00* | (2006.01) |
| *C07K 14/515* | (2006.01) |
| *C07K 14/52* | (2006.01) |
| *A61K 48/00* | (2006.01) |
| *C07K 14/71* | (2006.01) |
| *C07K 14/715* | (2006.01) |
| *A61K 39/00* | (2006.01) |

(52) U.S. Cl.
CPC ..... *C07K 14/715* (2013.01); *A61K 2039/55594* (2013.01); *A61K 38/1858* (2013.01); *A61K 39/001* (2013.01); *A61K 2039/5256* (2013.01); *C07K 14/515* (2013.01); *A61K 38/1866* (2013.01); *C07K 14/52* (2013.01); *A61K 48/005* (2013.01); *A61K 2039/53* (2013.01); *A61K 2039/55516* (2013.01); *C07K 14/71* (2013.01); *A61K 39/0011* (2013.01); *A61K 39/0005* (2013.01); *A61K 2039/5258* (2013.01); *A61K 39/0008* (2013.01)

USPC ... 514/8.1; 424/143.1; 424/145.1; 424/184.1; 424/185.1; 424/198.1; 424/278.1; 435/6.17; 514/7.6; 530/388.24

(58) Field of Classification Search
CPC . A61K 38/18; A61K 38/177; A61K 38/1866; A61K 2300/00; A61K 2039/53; A61K 2039/57; A61K 2039/555; A61L 27/3808; A61L 31/16; C07K 14/171; C08L 1/00
See application file for complete search history.

(56) References Cited

U.S. PATENT DOCUMENTS

| | | | | |
|---|---|---|---|---|
| 5,219,739 A | * | 6/1993 | Tischer et al. | 435/69.4 |
| 6,149,921 A | * | 11/2000 | Rodriguez et al. | 424/277.1 |
| 7,556,809 B2 | * | 7/2009 | Romero et al. | 424/185.1 |

FOREIGN PATENT DOCUMENTS

| | | | | |
|---|---|---|---|---|
| WO | WO 96-06641 | * | 3/1996 | A61K 47/48 |
| WO | WO 99/45018 | * | 9/1999 | C07H 21/02 |
| WO | WO 00/53219 | | 9/2000 | |

OTHER PUBLICATIONS

Muller et al., "Vascular Endothelial Growth Factor: Crystal Structure and Functional Mapping of the Kinase Domain Receptor Binding Site", Proc. Natl. Acad. Sci USA, vol. 94, No. 14, 7192-7197 (1997).
Asano et al., "An Anti-Human VEGF Monoclonal Antibody, MV833, that Exhibits Potent Anti-Tumor Activity In Vivo", Hybridoma, vol. 17, No. 2, 185-190 (1998).
Brekken et al., "Selective Inhibition of Vascular Endothelial Growth Factor (VEGF) Receptor 2 (KDR/Flk-1) Activity by a Monoclonal Anti-VEGF Antibody Blocks Tumor Growth in Mice", Cancer Research, vol. 60, No. 18, 5117-5124 (2000).
Muller et al., "VEGF and the Fab Fragment of a Humanized Neutralizing Antibody: Crystal Structure of the Complex at 2.4 Å Resolution and Mutational Analysis of the Interface", Structure, Current Biology Ltd., vol. 6, No. 9, 1153-1167 (1998).

(Continued)

*Primary Examiner* — Ja'Na Hines
(74) *Attorney, Agent, or Firm* — Hoffmann & Baron, LLP

(57) ABSTRACT

Application of oligonucleotide and polypeptide sequences of molecules of the family of the vascular permeability factor (VPF), their receptors, and co-receptors, as well as their modifications, in the active immunotherapy of pathologic entities in which course is associated to the increase of angiogenesis.
These procedures can be employed in the single or combined therapy for the treatment of cancer and its metastasis, acute and chronic inflammatory processes, infectious diseases, autoimmune diseases, diabetic and newborn retinopathies, organ transplant rejection, macular degeneration, neovascular glaucoma, hemangioma, and angiofibroma, among others.

4 Claims, No Drawings

(56) References Cited

OTHER PUBLICATIONS

Brekken et al., "VEGF-VEGF Receptor Complexes as Markers of Tumor Vascular Endothelium", Journal of Controlled Release, vol. 74, No. 1-3, 173-181 (2001).

Vitaliti et al., "Inhibition of Tumor Angiogenesis by a Single-Chain Antibody Directed Against Vascular Endothelial Growth Factor", Cancer Research, vol. 60, No. 16, 4311-4314 (2000).

Fuh et al., "Structure-Function Studies of Two Synthetic Anti-Vascular Endothelial Growth Factor Fabs and Comparison with the Avastin™ Fab", Journal of Biological Chemistry, vol. 281, No. 10, 6625-6631 (2006).

Jayson et al., "Molecular Imaging and Biological Evaluation of HuMV833 Anti-VEGF Antibody: Implications for Trial Design of Antiangiogenic Antibodies", Journal of the National Cancer Institute, vol. 94, No. 19, 1484-1493 (2002).

Davidoff, Andrew M. et al., "Bone Marrow-derived Cells Contribute to Tumor Neovasculature and, When Modified to Express an Angiogenesis Inhibitor, Can Restrict Tumor Growth in Mice", Clinical Cancer Research 2001, 7:2870-2879.

Prewitt, Marie et al., "Antivascular Endothelial Growth Factor Receptor (Fetal Liver Kinase 1) Monoclonal Antibody Inhibits Tumor Angiogenesis and Growth of Several Mouse and Human Tumors", Cancer Research 1999, 59:5209-5218.

Wei, Yu-quan et al., "Immunogene therapy of tumors with vaccine based on *Xenopus* homologous vascular endothelial growth factor as a model antigen", PNAS 2001, 98(20):11545-11550.

Stacker et al., "A Mutant Form of Vascular Endothelial Growth Factor (VEGF) that Lacks VEGF Receptor-2 Activation Retains the Ability to Induce Vascular Permeability", J Biol Chemistry, vol. 274, No. 49, Dec. 1999, pp. 34884-34892.

Dan Lu, et al., "Identification of the Residues in the Extracellular Region of KDR Important for Interaction With Vascular Endothelial Growth Factor and Neutralizing Anti-KDR Antibodies", J Biol Chemistry, vol. 275, No. 19, May 2000, pp. 14321-14330.

Gerhard Siemeister et al "The a-Helical Domain Near the Amino Terminus is Essential for Dimerization of Vascular Endothelial Growth Factor", J Biol Chemistry, vol. 273, No. 18, May 1998, pp. 11115-11120.

\* cited by examiner

```
                         SEQUENCE LISTING

<160> NUMBER OF SEQ ID NOS: 226

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
tggatccatg aactttctgc t                                             21

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
gaattcaccg cctcggcttg tc                                            22

<210> SEQ ID NO 3
<211> LENGTH: 21
<212> TYPE: DNA
<213> ORGANISM: Artificial Sequence
```

```
<220> FEATURE:
<223> OTHER INFORMATION: primer

<400> SEQUENCE: 3
tggatccatg aactttctgc t                                              21

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
ctggccttgt gcaggtgcga ttgccataat                                     30

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
attatggcaa tcgcacctgc acaaggccag                                     30

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gaattcaccg cctcggcttg tc                                             22

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
tggatccatg aactttctgc t                                              21

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gaattcaccg cctcggcttg tc                                             22

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
tggatccatg gagagcaagg tgctg                                          25
```

```
<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
gaattcacat cagcccactg gatgc                                          25

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cctctagatg tgcaaaagtg g                                              21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgagatcttc gggagcttcc                                                20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
gaagatctgt ataaggactt c                                              21

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
tagcggccgc ttaaacagg                                                 19

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
aggcctctac acctgccagg ca                                             22

<210> SEQ ID NO 16
<211> LENGTH: 20
<212> TYPE: DNA
<213> ORGANISM: Artificial Sequence
<220> FEATURE:
<223> OTHER INFORMATION: primer
```

-continued

<400> SEQUENCE: 16
cctaggttaa acaggaggag                                                        20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
cccgggatat ttataaagat c                                                      21

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
tagcggccgc ttaaacagg                                                         19

<210> SEQ ID NO 19
<211> LENGTH: 147
<212> TYPE: PRT
<213> ORGANISM: Homo Sapiens

<400> SEQUENCE: 147

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Glu Ile Glu Pro Glu
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
    130                 135                 140

Pro Arg Arg
145

<210> SEQ ID NO 20
<211> LENGTH: 444
<212> TYPE: DNA
<213> ORGANISM: Homo Sapiens

<400> SEQUENCE: 20
atgaactttc tgctgtcttg ggtgcattgg agccttgcct tgctgctcta cctccaccat          60
gccaagtggt cccaggctgc acccatggca gaaggaggag gcagaatca tcacgaagtg          120

```
gtgaagttca tggatgtcta tcagcgcagc tactgccatc caatcgagac cctggtggac      180
atcttccagg agtaccctga tgagatcgag tacatcttca agccatcctg tgtgcccctg      240
atgcgatgcg ggggctgctg caatgacgag ggcctggagt gtgtgcccac tgaggagtcc      300
aacatcacca tgcagattat gcggatcaaa cctcaccaag ccagcacat aggagagatg       360 agcttcctac agcacaacaa atgtgaatgc agaccaaaga agatagagc aagacaagaa       420 aaatgtgaca agccgaggcg gtga                                             444
```

<210> SEQ ID NO 21
<211> LENGTH: 147
<212> TYPE: PRT
<213> ORGANISM: Homo Sapiens

<400> SEQUENCE: 147

```
Met Asn Phe Leu Leu Ser Trp Val His Trp Ser Leu Ala Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
    65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Ala Ile Ala Pro Ala
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
    130                 135                 140

Pro Arg Arg
145
```

<210> SEQ ID NO 22
<211> LENGTH: 444
<212> TYPE: DNA
<213> ORGANISM: Homo Sapiens

<400> SEQUENCE: 22

```
atgaactttc tgctgtcttg ggtgcattgg agccttgcct tgctgctcta cctccaccat      60
gccaagtggt cccaggctgc acccatggca gaaggaggag gcagaatca tcacgaagtg      120 gtgaagttca tggatgtcta tcagcgcagc tactgccatc caatcgagac cctggtggac     180
atcttccagg agtaccctga tgagatcgag tacatcttca agccatcctg tgtgcccctg     240
atgcgatgcg ggggctgctg caatgacgag ggcctggagt gtgtgcccac tgaggagtcc     300
aacatcacca tgcagattat ggcaatcgca cctgcacaag ccagcacat aggagagatg      360 agcttcctac agcacaacaa atgtgaatgc agaccaaaga agatagagc aagacaagaa      420 aaatgtgaca agccgaggcg gtaa                                            444
```

<210> SEQ ID NO 23
<211> LENGTH: 314
<212> TYPE: PRT
<213> ORGANISM: Homo Sapiens

<400> SEQUENCE: 314

```
Met Glu Ser Lys Val Leu Leu Ala Val Ala Leu Trp Leu Cys Val Glu
  1               5                  10                  15

Thr Arg Ala Ala Ser Val Gly Leu Pro Ser Val Ser Leu Asp Leu Pro
             20                  25                  30

Arg Leu Ser Ile Gln Lys Asp Ile Leu Thr Ile Lys Ala Asn Thr Thr
         35                  40                  45

Leu Gln Ile Thr Cys Arg Gly Gln Arg Asp Leu Asp Trp Leu Trp Pro
     50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
                 85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met
305                 310
```

<210> SEQ ID NO 24
<211> LENGTH: 943
<212> TYPE: DNA
<213> ORGANISM: Homo Sapiens

<400> SEQUENCE: 24

| | |
|---|---|
| atggagagca aggtgctgct ggccgtcgcc ctgtggctct gcgtggagac ccgggccgcc | 60 |
| tctgtgggtt tgcctagtgt ttctcttgat ctgcccaggc tcagcataca aaaagacata | 120 |
| cttacaatta aggctaatac aactcttcaa attacttgca ggggacagag ggacttggac | 180 |
| tggctttggc ccaataatca gagtggcagt gagcaaaggg tggaggtgac tgagtgcagc | 240 |

```
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg taacagaat ttcctgggac     540 agcaagaagg gctttactat tcccagctac atgatcagct atgctggcat ggtcttctgt    600
gaagcaaaaa ttaatgatga agttaccag tctattatgt acatagttgt cgttgtaggg     660
tataggattt atgatgtggt tctgagtccg tctcatggaa ttgaactatc tgttggagaa    720
aagcttgtct taaattgtac agcaagaact gaactaaatg tggggattga cttcaactgg    780 gaatacccctt cttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tga                       943
```

<210> SEQ ID NO 25
<211> LENGTH: 611
<212> TYPE: PRT
<213> ORGANISM: Homo sapiens

<400> SEQUENCE: 611

```
Ala Lys Val Glu Ala Phe Phe Ile Ile Glu Gly Ala Gln Glu Lys Thr
 1               5                  10                  15

Asn Leu Glu Ile Ile Ile Leu Val Gly Thr Ala Val Ile Ala Met Phe
                20                  25                  30

Phe Trp Leu Leu Leu Val Ile Ile Leu Arg Thr Val Lys Arg Ala Asn
            35                  40                  45

Gly Gly Glu Leu Lys Thr Gly Tyr Leu Ser Ile Val Met Asp Pro Asp
        50                  55                  60

Glu Leu Pro Leu Asp Glu His Cys Glu Arg Leu Pro Tyr Asp Ala Ser
 65                  70                  75                  80

Lys Trp Glu Phe Pro Arg Asp Arg Leu Lys Leu Gly Lys Pro Leu Gly
                85                  90                  95

Arg Gly Ala Phe Gly Gln Val Ile Glu Ala Asp Ala Phe Gly Ile Asp
            100                 105                 110

Lys Thr Ala Thr Cys Arg Thr Val Ala Val Lys Met Leu Lys Glu Gly
        115                 120                 125

Ala Thr His Ser Glu His Arg Ala Leu Met Ser Glu Leu Lys Ile Leu
    130                 135                 140

Ile His Ile Gly His His Leu Asn Val Val Asn Leu Leu Gly Ala Cys
145                 150                 155                 160

Thr Lys Pro Gly Gly Pro Leu Met Val Ile Val Glu Phe Cys Lys Phe
                165                 170                 175

Gly Asn Leu Ser Thr Tyr Leu Arg Ser Lys Arg Asn Glu Phe Val Pro
            180                 185                 190

Tyr Lys Thr Lys Gly Ala Arg Phe Arg Gln Gly Lys Asp Tyr Val Gly
        195                 200                 205

Ala Ile Pro Val Asp Leu Lys Arg Arg Leu Asp Ser Ile Thr Ser Ser
    210                 215                 220

Gln Ser Ser Ala Ser Ser Gly Phe Val Glu Glu Lys Ser Leu Ser Asp
225                 230                 235                 240

Val Glu Glu Glu Glu Ala Pro Glu Asp Leu Tyr Lys Asp Phe Leu Thr
                245                 250                 255
```

Leu Glu His Leu Ile Cys Tyr Ser Phe Gln Val Ala Lys Gly Met Glu
                260                 265                 270

Phe Leu Ala Ser Arg Lys Cys Ile His Arg Asp Leu Ala Ala Arg Asn
            275                 280                 285

Ile Leu Leu Ser Glu Lys Asn Val Val Lys Ile Cys Asp Phe Gly Leu
        290                 295                 300

Ala Arg Asp Ile Tyr Lys Asp Pro Asp Tyr Val Arg Lys Gly Asp Ala
305                 310                 315                 320

Arg Leu Pro Leu Lys Trp Met Ala Pro Glu Thr Ile Phe Asp Arg Val
                325                 330                 335

Tyr Thr Ile Gln Ser Asp Val Trp Ser Phe Gly Val Leu Leu Trp Glu
            340                 345                 350

Ile Phe Ser Leu Gly Ala Ser Pro Tyr Pro Gly Val Lys Ile Asp Glu
        355                 360                 365

Glu Phe Cys Arg Arg Leu Lys Glu Gly Thr Arg Met Arg Ala Pro Asp
370                 375                 380

Tyr Thr Thr Pro Glu Met Tyr Gln Thr Met Leu Asp Cys Trp His Gly
385                 390                 395                 400

Glu Pro Ser Gln Arg Pro Thr Phe Ser Glu Leu Val Glu His Leu Gly
                405                 410                 415

Asn Leu Leu Gln Ala Asn Ala Gln Gln Asp Gly Lys Asp Tyr Ile Val
            420                 425                 430

Leu Pro Ile Ser Glu Thr Leu Ser Met Glu Glu Asp Ser Gly Leu Ser
        435                 440                 445

Leu Pro Thr Ser Pro Val Ser Cys Met Glu Glu Glu Glu Val Cys Asp
450                 455                 460

Pro Lys Phe His Tyr Asp Asn Thr Ala Gly Ile Ser Gln Tyr Leu Gln
465                 470                 475                 480

Asn Ser Lys Arg Lys Ser Arg Pro Val Ser Val Lys Thr Phe Glu Asp
                485                 490                 495

Ile Pro Leu Glu Glu Pro Glu Val Lys Val Ile Pro Asp Asp Asn Gln
            500                 505                 510

Thr Asp Ser Gly Met Val Leu Ala Ser Glu Glu Leu Lys Thr Leu Glu
        515                 520                 525

Asp Arg Thr Lys Leu Ser Pro Ser Phe Gly Gly Met Val Pro Ser Lys
530                 535                 540

Ser Arg Glu Ser Val Ala Ser Glu Gly Ser Asn Gln Thr Ser Gly Tyr
545                 550                 555                 560

Gln Ser Gly Tyr His Ser Asp Asp Thr Asp Thr Thr Val Tyr Ser Ser
                565                 570                 575

Glu Glu Ala Glu Leu Leu Lys Leu Ile Glu Ile Gly Val Gln Thr Gly
            580                 585                 590

Ser Thr Ala Gln Ile Leu Gln Pro Asp Ser Gly Thr Thr Leu Ser Ser
        595                 600                 605

Pro Pro Val
    610

<210> SEQ ID NO 26
<211> LENGTH: 1836
<212> TYPE: DNA
<213> ORGANISM: Homo Sapiens

<400> SEQUENCE: 1836
gcaaaagtgg aggcattttt cataatagaa ggtgcccagg aaaagacgaa cttggaaatc    60

```
attattctag taggcacggc ggtgattgcc atgttcttct ggctacttct tgtcatcatc    120
ctacggaccg ttaagcgggc caatggaggg gaactgaaga caggctactt gtccatcgtc    180
atggatccag atgaactccc attggatgaa cattgtgaac gactgcctta tgatgccagc    240
aaatgggaat tccccagaga ccggctgaag ctaggtaagc tccttggccg tggtgccttt    300
ggccaagtga ttgaagcaga tgcctttgga attgacaaga cagcaacttg caggacagta    360
gcagtcaaaa tgttgaaaga aggagcaaca cacagtgagc atcgagctct catgtctgaa    420
ctcaagatcc tcattcatat tggtcaccat ctcaatgtgg tcaaccttct aggtgcctgt    480
accaagccag agggccact catggtgatt gtggaattct gcaaatttgg aaacctgtcc    540
acttacctga ggagcaagag aaatgaattt gtcccctaca agaccaaagg ggcacgattc    600
cgtcaaggga aagactacgt ggagcaatc cctgtggatc tgaaacggcg cttggacagc    660
atcaccagta gccagagctc agccagctct ggatttgtgg aggagaagtc cctcagtgat    720
gtagaagaag aggaagctcc tgaagatctg tataaggact tcctgacctt ggagcatctc    780
atctgttaca gcttccaagt ggctaagggc atggagttct tggcatcgcg aaagtgtatc    840
cacagggacc tggcggcacg aaatatcctc ttatcggaga gaacgtggt taaaatctgt    900
gactttggct tggcccggga tatttataaa gatccagatt atgtcagaaa aggagatgct    960
cgcctccctt tgaatggat ggccccagaa acaattttg acagagtgta cacaatccag   1020
agtgacgtct ggtcttttgg tgttttgctg tgggaaatat tttccttagg tgcttctcca   1080
tatcctgggg taaagattga tgaagaattt gtaggcgat tgaaagaagg aactagaatg   1140
agggcccctg attatactac accagaaatg taccagacca tgctggactg ctggcacggg   1200
gagcccagtc agagacccac gttttcagag ttggtggaac attgggaaa tctcttgcaa   1260
gctaatgctc agcaggatgg caaagactac attgttcttc cgatatcaga gactttgagc   1320
atggaagagg attctggact ctctctgcct acctcacctg tttcctgtat ggaggaggag   1380
gaagtatgtg accccaaatt ccattatgac aacacagcag gaatcagtca gtatctgcag   1440
aacagtaagc gaaagagccg gcctgtgagt gtaaaaacat tgaagatat cccgttagaa   1500
gaaccagaag taaagtaat cccagatgac aaccagacgg acagtggtat ggttcttgcc   1560
tcagaagagc tgaaaacttt ggaagacaga accaaattat ctccatcttt tggtggaatg   1620
gtgcccagca aagcaggga gtctgtggca tctgaaggct caaaccagac aagcggctac   1680
cagtccggat atcactccga tgacacagac accaccgtgt actccagtga ggaagcagaa   1740
cttttaaagc tgatagagat tggagtgcaa accggtagca cagcccagat tctccagcct   1800
gactcgggga ccacactgag ctctcctcct gtttaa                             1836
```

<210> SEQ ID NO 27
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 27

Leu Leu Ser Trp Val His Trp Ser Leu
 1               5

<210> SEQ ID NO 28
<211> LENGTH: 9
<212> TYPE: PRT
<213> ORGANISM: Artificial Sequence

```
<220> FEATURE:
<223> OTHER INFORMATION: VEGF-A derived peptides

<400> SEQUENCE: 28

Ala Leu Leu Leu Tyr Leu His His Ala
 1               5

<210> SEQ ID NO 29
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 29

Trp Ser Leu Ala Leu Leu Leu Tyr Leu
 1               5

<210> SEQ ID NO 30
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 30

Phe Leu Gln His Asn Lys Cys Glu Cys
 1               5

<210> SEQ ID NO 31
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 31

Trp Val His Trp Ser Leu Ala Leu Leu
 1               5

<210> SEQ ID NO 32
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 32

Phe Leu Leu Ser Trp Val His Trp Ser
 1               5

<210> SEQ ID NO 33
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 33

Arg Gln Leu Glu Leu Asn Glu Arg Thr
 1               5

<210> SEQ ID NO 34
<211> LENGTH: 9
<212> TYPE: PRT
<213> ORGANISM: Artificial Sequence
<220> FEATURE:
```

```
<223> OTHER INFORMATION: VEGF-A derived peptides

<400> SEQUENCE: 34

Asn Ile Thr Met Gln Ile Met Arg Ile
 1               5

<210> SEQ ID NO 35
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 35

Tyr Cys His Pro Ile Glu Thr Leu Val
 1               5

<210> SEQ ID NO 36
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 36

Ile Glu Tyr Ile Phe Lys Pro Ser Cys
 1               5

<210> SEQ ID NO 37
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 37

Leu Leu Leu Ala Ala Leu Leu Gln Leu
 1               5

<210> SEQ ID NO 38
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 38

Gln Leu Ala Pro Ala Gln Ala Pro Val
 1               5

<210> SEQ ID NO 39
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 39

Gln Leu Val Pro Ser Cys Val Thr Val
 1               5

<210> SEQ ID NO 40
<211> LENGTH: 9
<212> TYPE: PRT
<213> ORGANISM: Artificial Sequence
<220> FEATURE:
<223> OTHER INFORMATION: VEGF-B derived peptides
```

```
<400> SEQUENCE: 40

Leu Met Gly Thr Val Ala Lys Gln Leu
 1               5

<210> SEQ ID NO 41
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 41

Leu Leu Ala Ala Leu Leu Gln Leu Ala
 1               5

<210> SEQ ID NO 42
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 42

Leu Leu Gln Leu Ala Pro Ala Gln Ala
 1               5

<210> SEQ ID NO 43
<211> LENGTH: 8
<212> TYPE: PRT
<213> ORGANISM: Artificial Sequence
<220> FEATURE:
<223> OTHER INFORMATION: VEGF-B derived peptides

<400> SEQUENCE: 43

Trp Ser Trp Ile Asp Val Tyr Thr
 1               5

<210> SEQ ID NO 44
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 44

Cys Val Pro Thr Gly Gln His Gln Val
 1               5

<210> SEQ ID NO 45
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 45

Lys Gln Leu Val Pro Ser Cys Val Thr
 1               5

<210> SEQ ID NO 46
<211> LENGTH: 8
<212> TYPE: PRT
<213> ORGANISM: Artificial Sequence
<220> FEATURE:
<223> OTHER INFORMATION: VEGF-B derived peptides
```

-continued

<400> SEQUENCE: 46

Trp Val Pro Leu Thr Val Glu Leu
 1               5

<210> SEQ ID NO 47
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 47

Tyr Leu Ser Lys Thr Leu Phe Glu Ile
 1               5

<210> SEQ ID NO 48
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 48

Thr Leu Phe Glu Ile Thr Val Pro Leu
 1               5

<210> SEQ ID NO 49
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 49

Val Leu Tyr Pro Glu Tyr Trp Lys Met
 1               5

<210> SEQ ID NO 50
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 50

Cys Met Asn Thr Ser Thr Ser Tyr Leu
 1               5

<210> SEQ ID NO 51
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 51

Lys Leu Phe Pro Ser Gln Cys Gly Ala
 1               5

<210> SEQ ID NO 52
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 52

```
Leu Leu Gly Phe Phe Ser Val Ala Cys
  1               5

<210> SEQ ID NO 53
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 53

Ser Leu Pro Ala Thr Leu Pro Gln Cys
  1               5

<210> SEQ ID NO 54
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 54

Gly Leu Gln Cys Met Asn Thr Ser Thr
  1               5

<210> SEQ ID NO 55
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 55

Ala Ala Phe Glu Ser Gly Leu Asp Leu
  1               5

<210> SEQ ID NO 56
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 56

Glu Gln Leu Arg Ser Val Ser Ser Val
  1               5

<210> SEQ ID NO 57
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 57

Phe Met Met Leu Tyr Val Gln Leu Val
  1               5

<210> SEQ ID NO 58
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 58
```

Lys Leu Trp Arg Cys Arg Leu Arg Leu
 1               5

<210> SEQ ID NO 59
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 59

Gln Leu Phe Glu Ile Ser Val Pro Leu
 1               5

<210> SEQ ID NO 60
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 60

Tyr Ile Ser Lys Gln Leu Phe Glu Ile
 1               5

<210> SEQ ID NO 61
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 61

Cys Met Asn Thr Ser Thr Ser Tyr Ile
 1               5

<210> SEQ ID NO 62
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 62

Val Leu Gln Glu Glu Asn Pro Leu Ala
 1               5

<210> SEQ ID NO 63
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 63

Trp Val Val Val Asn Val Phe Met Met
 1               5

<210> SEQ ID NO 64
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 64

Val Asn Val Phe Met Met Leu Tyr Val

```
<210> SEQ ID NO 65
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 65

Ser Leu Ile Cys Met Asn Thr Ser Thr
  1               5

<210> SEQ ID NO 66
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 66

Cys Val Leu Gln Glu Glu Asn Pro Leu
  1               5

<210> SEQ ID NO 67
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 67

Arg Leu Phe Pro Cys Phe Leu Gln Leu
  1               5

<210> SEQ ID NO 68
<211> LENGTH: 8
<212> TYPE: PRT
<213> ORGANISM: Artificial Sequence
<220> FEATURE:
<223> OTHER INFORMATION: PLGF derived peptides

<400> SEQUENCE: 68

Trp Ser Glu Tyr Pro Ser Glu Val
  1               5

<210> SEQ ID NO 69
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 69

Val Met Arg Leu Phe Pro Cys Phe Leu
  1               5

<210> SEQ ID NO 70
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 70

Arg Ala Leu Glu Arg Leu Val Asp Val
  1               5
```

<210> SEQ ID NO 71
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 71

Val Glu Leu Thr Phe Ser Gln His Val
 1               5

<210> SEQ ID NO 72
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 72

Ala Val Pro Pro Gln Gln Trp Ala Leu
 1               5

<210> SEQ ID NO 73
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 73

Leu Gln Leu Leu Ala Gly Leu Ala Leu
 1               5

<210> SEQ ID NO 74
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 74

Arg Ser Gly Asp Arg Pro Ser Tyr Val
 1               5

<210> SEQ ID NO 75
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 75

Leu Leu Ala Gly Leu Ala Leu Pro Ala
 1               5

<210> SEQ ID NO 76
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 76

Cys Val Pro Val Glu Thr Ala Asn Val
 1               5

```
<210> SEQ ID NO 77
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 77

Leu Leu Ser Trp Val His Trp Ser Leu
  1               5

<210> SEQ ID NO 78
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 78

Ala Leu Leu Leu Tyr Leu His His Ala
  1               5

<210> SEQ ID NO 79
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 79

Trp Val His Trp Ser Leu Ala Leu Leu
  1               5

<210> SEQ ID NO 80
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 80

Ser Leu Ala Leu Leu Leu Tyr Leu His
  1               5

<210> SEQ ID NO 81
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 81

Ser Tyr Cys His Pro Ile Glu Thr Leu
  1               5

<210> SEQ ID NO 82
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 82

Asn Ile Thr Met Gln Ile Met Arg Ile
  1               5
```

```
<210> SEQ ID NO 83
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 83

Phe Leu Leu Ser Trp Val His Trp Ser
 1               5

<210> SEQ ID NO 84
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 84

Trp Ser Leu Ala Leu Leu Leu Tyr Leu
 1               5

<210> SEQ ID NO 85
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 85

His Pro Ile Glu Thr Leu Val Asp Ile
 1               5

<210> SEQ ID NO 86
<211> LENGTH: 9
<212> TYPE: PRT
<213> ORGANISM: Artificial Sequence
<220> FEATURE:
<223> OTHER INFORMATION: VEGF-A derived peptides

<400> SEQUENCE: 86

Cys Asn Asp Glu Gly Leu Glu Cys Val
 1               5

<210> SEQ ID NO 87
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 87

Leu Leu Leu Ala Ala Leu Leu Gln Leu
 1               5

<210> SEQ ID NO 88
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 88

Gln Leu Ala Pro Ala Gln Ala Pro Val
 1               5

<210> SEQ ID NO 89
```

```
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 89

Gln Leu Val Pro Ser Cys Val Thr Val
 1               5

<210> SEQ ID NO 90
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 90

Val Val Val Pro Leu Thr Val Glu Leu
 1               5

<210> SEQ ID NO 91
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 91

Leu Leu Arg Arg Leu Leu Leu Ala Ala
 1               5

<210> SEQ ID NO 92
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 92

Leu Leu Ala Ala Leu Leu Gln Leu Ala
 1               5

<210> SEQ ID NO 93
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 93

Phe Leu Arg Cys Gln Gly Arg Gly Leu
 1               5

<210> SEQ ID NO 94
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 94

Leu Thr Val Glu Leu Met Gly Thr Val
 1               5

<210> SEQ ID NO 95
<211> LENGTH: 9
```

```
<212> TYPE: PRT
<213> ORGANISM: Artificial Sequence
<220> FEATURE:
<223> OTHER INFORMATION: VEGF-B derived peptides

<400> SEQUENCE: 95

Leu Arg Arg Leu Leu Leu Ala Ala Leu
 1               5

<210> SEQ ID NO 96
<211> LENGTH: 9
<212> TYPE: PRT
<213> ORGANISM: Artificial Sequence
<220> FEATURE:
<223> OTHER INFORMATION: VEGF-B derived peptides

<400> SEQUENCE: 96

Leu Met Gly Thr Val Ala Lys Gln Leu
 1               5

<210> SEQ ID NO 97
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 97

Thr Leu Phe Glu Ile Thr Val Pro Leu
 1               5

<210> SEQ ID NO 98
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 98

Asp Leu Glu Glu Gln Leu Arg Ser Val
 1               5

<210> SEQ ID NO 99
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 99

Tyr Leu Ser Lys Thr Leu Phe Glu Ile
 1               5

<210> SEQ ID NO 100
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 100

Ala Leu Leu Pro Gly Pro Arg Glu Ala
 1               5

<210> SEQ ID NO 101
<211> LENGTH: 9
<212> TYPE: PRT
```

```
<213> ORGANISM: Artificial Sequence
<220> FEATURE:
<223> OTHER INFORMATION: VEGF-C derived peptides

<400> SEQUENCE: 101

Cys Met Asn Thr Ser Thr Ser Tyr Leu
  1               5

<210> SEQ ID NO 102
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 102

Asp Ile Cys Gly Pro Asn Lys Glu Leu
  1               5

<210> SEQ ID NO 103
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 103

Ala Ala Ala Ala Phe Glu Ser Gly Leu
  1               5

<210> SEQ ID NO 104
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 104

Ala Ala Phe Glu Ser Gly Leu Asp Leu
  1               5

<210> SEQ ID NO 105
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 105

Val Leu Tyr Pro Glu Tyr Trp Lys Met
  1               5

<210> SEQ ID NO 106
<211> LENGTH: 9
<212> TYPE: PRT
<213> ORGANISM: Artificial Sequence
<220> FEATURE:
<223> OTHER INFORMATION: VEGF-C derived peptides

<400> SEQUENCE: 106

Ile Ile Arg Arg Ser Leu Pro Ala Thr
  1               5

<210> SEQ ID NO 107
<211> LENGTH: 9
<212> TYPE: PRT
<213> ORGANISM: Artificial Sequence
```

```
<220> FEATURE:
<223> OTHER INFORMATION: VEGF-D derived peptides

<400> SEQUENCE: 107

Phe Met Met Leu Tyr Val Gln Leu Val
 1               5

<210> SEQ ID NO 108
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 108

Gln Leu Phe Glu Ile Ser Val Pro Leu
 1               5

<210> SEQ ID NO 109
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 109

Tyr Ile Ser Lys Gln Leu Phe Glu Ile
 1               5

<210> SEQ ID NO 110
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 110

Lys Leu Trp Arg Cys Arg Leu Arg Leu
 1               5

<210> SEQ ID NO 111
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 111

Arg Ala Ala Ser Ser Leu Glu Glu Leu
 1               5

<210> SEQ ID NO 112
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 112

Ser Leu Glu Glu Leu Leu Arg Ile Thr
 1               5

<210> SEQ ID NO 113
<211> LENGTH: 9
<212> TYPE: PRT
<213> ORGANISM: Artificial Sequence
<220> FEATURE:
```

```
<223> OTHER INFORMATION: VEGF-D derived peptides

<400> SEQUENCE: 113

Ala Thr Phe Tyr Asp Ile Glu Thr Leu
 1               5

<210> SEQ ID NO 114
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 114

Glu Ile Ser Val Pro Leu Thr Ser Val
 1               5

<210> SEQ ID NO 115
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 115

Ser Leu Ile Cys Met Asn Thr Ser Thr
 1               5

<210> SEQ ID NO 116
<211> LENGTH: 9
<212> TYPE: PRT
<213> ORGANISM: Artificial Sequence
<220> FEATURE:
<223> OTHER INFORMATION: VEGF-D derived peptides

<400> SEQUENCE: 116

Val Pro Leu Thr Ser Val Pro Glu Leu
 1               5

<210> SEQ ID NO 117
<211> LENGTH: 8
<212> TYPE: PRT
<213> ORGANISM: Artificial Sequence
<220> FEATURE:
<223> OTHER INFORMATION: PLGF derived peptides

<400> SEQUENCE: 117

Ala Leu Glu Arg Leu Val Asp Trp
 1               5

<210> SEQ ID NO 118
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 118

Arg Leu Phe Pro Cys Phe Leu Gln Leu
 1               5

<210> SEQ ID NO 119
<211> LENGTH: 9
<212> TYPE: PRT
<213> ORGANISM: Artificial Sequence
<220> FEATURE:
<223> OTHER INFORMATION: PLGF derived peptides
```

```
<400> SEQUENCE: 119

Arg Ala Leu Glu Arg Leu Val Asp Val
 1               5

<210> SEQ ID NO 120
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 120

Leu Leu Ala Gly Leu Ala Leu Pro Ala
 1               5

<210> SEQ ID NO 121
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 121

Leu Ala Gly Leu Ala Leu Pro Ala Val
 1               5

<210> SEQ ID NO 122
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 122

Val Met Arg Leu Phe Pro Cys Phe Leu
 1               5

<210> SEQ ID NO 123
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 123

Cys Phe Leu Gln Leu Leu Ala Gly Leu
 1               5

<210> SEQ ID NO 124
<211> LENGTH: 9
<212> TYPE: PRT
<213> ORGANISM: Artificial Sequence
<220> FEATURE:
<223> OTHER INFORMATION: PLGF derived peptides

<400> SEQUENCE: 124

Gln Leu Leu Ala Gly Leu Ala Leu Pro
 1               5

<210> SEQ ID NO 125
<211> LENGTH: 9
<212> TYPE: PRT
<213> ORGANISM: Artificial Sequence
<220> FEATURE:
<223> OTHER INFORMATION: PLGF derived peptides
```

```
<400> SEQUENCE: 125

Ser Ala Gly Asn Gly Ser Ser Glu Val
  1               5

<210> SEQ ID NO 126
<211> LENGTH: 8
<212> TYPE: PRT
<213> ORGANISM: Artificial Sequence
<220> FEATURE:
<223> OTHER INFORMATION: PLGF derived peptides

<400> SEQUENCE: 126

Trp Ser Glu Tyr Pro Ser Glu Val
  1               5

<210> SEQ ID NO 127
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 127

Phe Leu Tyr Arg Asp Val Thr Trp Ile
  1               5

<210> SEQ ID NO 128
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 128

Val Leu Leu Trp Glu Ile Phe Ser Leu
  1               5

<210> SEQ ID NO 129
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 129

Lys Leu Leu Arg Gly His Thr Leu Val
  1               5

<210> SEQ ID NO 130
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 130

Gly Leu Leu Thr Cys Glu Ala Thr Val
  1               5

<210> SEQ ID NO 131
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 131
```

Thr Leu Phe Trp Leu Leu Leu Thr Leu
 1               5

<210> SEQ ID NO 132
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 132

Ile Leu Leu Ser Glu Asn Asn Val Val
 1               5

<210> SEQ ID NO 133
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 133

Thr Leu Asn Leu Thr Ile Met Asn Val
 1               5

<210> SEQ ID NO 134
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 134

Cys Val Ala Ala Thr Leu Phe Trp Leu
 1               5

<210> SEQ ID NO 135
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 135

Leu Leu Ser Ile Lys Gln Ser Asn Val
 1               5

<210> SEQ ID NO 136
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 136

Ser Leu Gln Asp Ser Gly Thr Tyr Ala
 1               5

<210> SEQ ID NO 137
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 137

Val Leu Leu Trp Glu Ile Phe Ser Leu
1               5

<210> SEQ ID NO 138
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 138

Ser Leu Gln Asp Gln Gly Asp Tyr Val
1               5

<210> SEQ ID NO 139
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 139

Val Leu Leu Ala Val Ala Leu Trp Leu
1               5

<210> SEQ ID NO 140
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 140

Ala Met Phe Phe Trp Leu Leu Leu Val
1               5

<210> SEQ ID NO 141
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 141

Val Ile Ala Met Phe Phe Trp Leu Leu
1               5

<210> SEQ ID NO 142
<211> LENGTH: 8
<212> TYPE: PRT
<213> ORGANISM: Artificial Sequence
<220> FEATURE:
<223> OTHER INFORMATION: VEGFR-2 derived peptides

<400> SEQUENCE: 142

Ile Leu Leu Ser Glu Lys Asn Trp
1               5

<210> SEQ ID NO 143
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 143

Leu Leu Ala Val Ala Leu Trp Leu Cys

```
<210> SEQ ID NO 144
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 144

Lys Asn Leu Asp Thr Leu Trp Lys Leu
 1               5

<210> SEQ ID NO 145
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 145

Ala Val Ile Ala Met Phe Phe Trp Leu
 1               5

<210> SEQ ID NO 146
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 146

Leu Leu Leu Val Ile Ile Leu Arg Thr
 1               5

<210> SEQ ID NO 147
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 147

Val Leu Leu Trp Glu Ile Phe Ser Leu
 1               5

<210> SEQ ID NO 148
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 148

Arg Leu Leu Glu Glu Lys Ser Gly Val
 1               5

<210> SEQ ID NO 149
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 149

Val Leu Trp Pro Asp Gly Gln Glu Val
 1               5
```

<210> SEQ ID NO 150
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 150

Asn Leu Thr Asp Leu Leu Val Asn Val
 1               5

<210> SEQ ID NO 151
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 151

Lys Gln Ala Glu Arg Gly Lys Trp Val
 1               5

<210> SEQ ID NO 152
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 152

Gly Val Ile Ala Val Phe Phe Trp Val
 1               5

<210> SEQ ID NO 153
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 153

Lys Leu Val Ile Gln Asn Ala Asn Val
 1               5

<210> SEQ ID NO 154
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 154

Ala Leu Trp Asn Ser Ala Ala Gly Leu
 1               5

<210> SEQ ID NO 155
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 155

Thr Leu Ser Leu Ser Ile Pro Arg Val
 1               5

<210> SEQ ID NO 156
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 156

Ser Gln His Asp Leu Gly Ser Tyr Val
 1               5

<210> SEQ ID NO 157
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 157

Gly Leu Leu Arg Phe Val Thr Ala Val
 1               5

<210> SEQ ID NO 158
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 158

Val Leu Leu Gly Ala Val Cys Gly Val
 1               5

<210> SEQ ID NO 159
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 159

Trp Met Pro Glu Asn Ile Arg Leu Val
 1               5

<210> SEQ ID NO 160
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 160

Gly Ile Leu Ser Met Val Phe Tyr Thr
 1               5

<210> SEQ ID NO 161
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 161

Leu Leu Cys Ala Val Leu Ala Leu Val
 1               5

```
<210> SEQ ID NO 162
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 162

Val Leu Leu His Lys Ser Leu Lys Leu
  1               5

<210> SEQ ID NO 163
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 163

Gly Met Leu Gly Met Val Ser Gly Leu
  1               5

<210> SEQ ID NO 164
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 164

Phe Gln Leu Thr Gly Gly Thr Thr Val
  1               5

<210> SEQ ID NO 165
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 165

Val Leu Ala Thr Glu Lys Pro Thr Val
  1               5

<210> SEQ ID NO 166
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 166

Gly Pro Phe Leu Phe Ile Lys Phe Val
  1               5

<210> SEQ ID NO 167
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 167

Trp Met Tyr Asp His Ala Lys Trp Leu
  1               5

<210> SEQ ID NO 168
```

```
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 168

Ile Leu Gln Phe Leu Ile Phe Asp Leu
 1               5

<210> SEQ ID NO 169
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 169

Tyr Leu Gln Val Asp Leu Arg Phe Leu
 1               5

<210> SEQ ID NO 170
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 170

Ala Leu Tyr Phe Ser Arg His Gln Val
 1               5

<210> SEQ ID NO 171
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 171

Asn Met Leu Gly Met Leu Ser Gly Leu
 1               5

<210> SEQ ID NO 172
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 172

Trp Leu Tyr Thr Leu Asp Pro Ile Leu
 1               5

<210> SEQ ID NO 173
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 173

Asp Ile Trp Asp Gly Ile Pro His Val
 1               5

<210> SEQ ID NO 174
<211> LENGTH: 9
```

```
<212> TYPE: PRT
<213> ORGANISM: Artificial Sequence
<220> FEATURE:
<223> OTHER INFORMATION: NRP-2 derived peptides

<400> SEQUENCE: 174

Lys Met Glu Ile Ile Leu Gln Phe Leu
 1               5

<210> SEQ ID NO 175
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 175

Val Leu Asn Lys Leu His Ala Pro Leu
 1               5

<210> SEQ ID NO 176
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 176

Leu Leu Gly Ala Thr Cys Ala Gly Leu
 1               5

<210> SEQ ID NO 177
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 177

Thr Leu Phe Trp Leu Leu Leu Thr Leu
 1               5

<210> SEQ ID NO 178
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 178

Val Leu Leu Trp Glu Ile Phe Ser Leu
 1               5

<210> SEQ ID NO 179
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 179

Ile Leu Gly Pro Gly Ser Ser Thr Leu
 1               5

<210> SEQ ID NO 180
<211> LENGTH: 9
<212> TYPE: PRT
```

<213> ORGANISM: Artificial Sequence
<220> FEATURE:
<223> OTHER INFORMATION: VEGFR-1 derived peptides

<400> SEQUENCE: 180

Leu Leu Cys Ala Leu Leu Ser Cys Leu
 1               5

<210> SEQ ID NO 181
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 181

Gly Leu Leu Thr Cys Glu Ala Thr Val
 1               5

<210> SEQ ID NO 182
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 182

Leu Leu Arg Gly His Thr Leu Val Leu
 1               5

<210> SEQ ID NO 183
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 183

Ala Leu Met Thr Glu Leu Lys Ile Leu
 1               5

<210> SEQ ID NO 184
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 184

Lys Leu Leu Arg Gly His Thr Leu Val
 1               5

<210> SEQ ID NO 185
<211> LENGTH: 9
<212> TYPE: PRT
<213> ORGANISM: Artificial Sequence
<220> FEATURE:
<223> OTHER INFORMATION: VEGFR-1 derived peptides

<400> SEQUENCE: 185

Thr Leu Asn Leu Thr Ile Met Asn Val
 1               5

<210> SEQ ID NO 186
<211> LENGTH: 9
<212> TYPE: PRT
<213> ORGANISM: Artificial Sequence

```
<220> FEATURE:
<223> OTHER INFORMATION: VEGFR-1 derived peptides

<400> SEQUENCE: 186

Ile Leu Leu Ser Glu Asn Asn Val Val
 1               5

<210> SEQ ID NO 187
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 187

Val Leu Leu Trp Glu Ile Phe Ser Leu
 1               5

<210> SEQ ID NO 188
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 188

Leu Leu Val Ile Ile Leu Arg Thr Val
 1               5

<210> SEQ ID NO 189
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 189

Gly Leu Phe Cys Lys Thr Leu Thr Ile
 1               5

<210> SEQ ID NO 190
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 190

Ser Ile Met Tyr Ile Val Val Val Val
 1               5

<210> SEQ ID NO 191
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 191

Ile Ile Leu Val Gly Thr Ala Val Ile
 1               5

<210> SEQ ID NO 192
<211> LENGTH: 9
<212> TYPE: PRT
<213> ORGANISM: Artificial Sequence
<220> FEATURE:
```

```
<223> OTHER INFORMATION: VEGFR-2 derived peptides

<400> SEQUENCE: 192

Ala Leu Met Ser Glu Leu Lys Ile Leu
 1               5

<210> SEQ ID NO 193
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 193

Ala Ala Ser Val Gly Leu Pro Ser Val
 1               5

<210> SEQ ID NO 194
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 194

Ser Ile Ser Asn Leu Asn Val Ser Leu
 1               5

<210> SEQ ID NO 195
<211> LENGTH: 9
<212> TYPE: PRT
<213> ORGANISM: Artificial Sequence
<220> FEATURE:
<223> OTHER INFORMATION: VEGFR-2 derived peptides

<400> SEQUENCE: 195

Ala Met Phe Phe Trp Leu Leu Leu Val
 1               5

<210> SEQ ID NO 196
<211> LENGTH: 8
<212> TYPE: PRT
<213> ORGANISM: Artificial Sequence
<220> FEATURE:
<223> OTHER INFORMATION: VEGFR-2 derived peptides

<400> SEQUENCE: 196

Ile Leu Leu Ser Glu Lys Asn Trp
 1               5

<210> SEQ ID NO 197
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 197

Val Leu Leu Trp Glu Ile Phe Ser Leu
 1               5

<210> SEQ ID NO 198
<211> LENGTH: 9
<212> TYPE: PRT
<213> ORGANISM: Artificial Sequence
<220> FEATURE:
<223> OTHER INFORMATION: VEGFR-3 derived peptides
```

<400> SEQUENCE: 198

Ser Ile Pro Gly Leu Asn Val Thr Leu
 1               5

<210> SEQ ID NO 199
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 199

Asn Leu Thr Asp Leu Leu Val Asn Val
 1               5

<210> SEQ ID NO 200
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 200

Val Leu Trp Pro Asp Gly Gln Glu Val
 1               5

<210> SEQ ID NO 201
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 201

Leu Leu Pro Arg Lys Ser Leu Glu Leu
 1               5

<210> SEQ ID NO 202
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 202

Ala Leu Trp Asn Ser Ala Ala Gly Leu
 1               5

<210> SEQ ID NO 203
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 203

Ile Met Asp Pro Gly Glu Val Pro Leu
 1               5

<210> SEQ ID NO 204
<211> LENGTH: 9
<212> TYPE: PRT
<213> ORGANISM: Artificial Sequence
<220> FEATURE:
<223> OTHER INFORMATION: VEGFR-3 derived peptides

```
<400> SEQUENCE: 204

Arg Leu Trp Leu Cys Leu Gly Leu Leu
 1               5

<210> SEQ ID NO 205
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 205

Leu Ile Tyr Phe Tyr Val Thr Thr Ile
 1               5

<210> SEQ ID NO 206
<211> LENGTH: 9
<212> TYPE: PRT
<213> ORGANISM: Artificial Sequence
<220> FEATURE:
<223> OTHER INFORMATION: VEGFR-3 derived peptides

<400> SEQUENCE: 206

Leu Leu Glu Gly Gln Pro Val Leu Leu
 1               5

<210> SEQ ID NO 207
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 207

Val Leu Leu Gly Ala Val Cys Gly Val
 1               5

<210> SEQ ID NO 208
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 208

Gly Leu Leu Arg Phe Val Thr Ala Val
 1               5

<210> SEQ ID NO 209
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 209

Leu Leu Cys Ala Val Leu Ala Leu Val
 1               5

<210> SEQ ID NO 210
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 210
```

```
Gly Met Leu Gly Met Val Ser Gly Leu
  1               5

<210> SEQ ID NO 211
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 211

Ala Leu Gly Val Leu Leu Gly Ala Val
  1               5

<210> SEQ ID NO 212
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 212

Val Leu Leu His Lys Ser Leu Lys Leu
  1               5

<210> SEQ ID NO 213
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 213

Val Leu Ala Thr Glu Lys Pro Thr Val
  1               5

<210> SEQ ID NO 214
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 214

Gln Leu Thr Gly Gly Thr Thr Val Leu
  1               5

<210> SEQ ID NO 215
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 215

Val Leu Leu Gly Ala Val Cys Gly Val
  1               5

<210> SEQ ID NO 216
<211> LENGTH: 9
<212> TYPE: PRT
<213> ORGANISM: Artificial Sequence
<220> FEATURE:
<223> OTHER INFORMATION: NRP-1 derived peptides

<400> SEQUENCE: 216
```

```
Gly Leu Leu Arg Phe Val Thr Ala Val
  1               5
```

<210> SEQ ID NO 217
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 217

```
Asn Met Leu Gly Met Leu Ser Gly Leu
  1               5
```

<210> SEQ ID NO 218
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 218

```
Ile Leu Gln Phe Leu Ile Phe Asp Leu
  1               5
```

<210> SEQ ID NO 219
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 219

```
Asp Ile Trp Asp Gly Ile Pro His Val
  1               5
```

<210> SEQ ID NO 220
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 220

```
Tyr Leu Gln Val Asp Leu Arg Phe Leu
  1               5
```

<210> SEQ ID NO 221
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 221

```
Thr Leu Asp Pro Ile Leu Ile Thr Ile
  1               5
```

<210> SEQ ID NO 222
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 222

```
Ile Leu Ala Lys Pro Lys Met Glu Ile
```

```
<210> SEQ ID NO 223
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 223

Val Leu Asn Lys Leu His Ala Pro Leu
  1               5

<210> SEQ ID NO 224
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 224

Leu Leu Gly Ala Thr Cys Ala Gly Leu
  1               5

<210> SEQ ID NO 225
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 225

Ala Leu Tyr Phe Ser Arg His Gln Val
  1               5

<210> SEQ ID NO 226
<211> LENGTH: 9
<212> TYPE: PRT
<213> ORGANISM: Artificial Sequence
<220> FEATURE:
<223> OTHER INFORMATION: NRP-2 derived peptides

<400> SEQUENCE: 226

Gly Ile Gly Met Arg Leu Glu Val Leu
  1               5
```

ACTIVE ANTIANGIOGENIC THERAPY

CROSS-REFERENCE TO RELATED APPLICATION

This application is a divisional of U.S. application Ser. No. 11/787,522, filed Apr. 17, 2007, which is a divisional of U.S. application Ser. No. 10/511,384, filed Oct. 15, 2004, now U.S. Pat. No. 7,556,809, which is a U.S. National Phase Application of International Application No. PCT/CU03/00004 filed on Apr. 11, 2003, which asserts priority to Cuban Application No. CU2002/0076 filed on Apr. 15, 2002. The foregoing applications and patents are hereby incorporated by reference in their entirety herein.

BACKGROUND OF THE INVENTION

The present invention is related with the field of biotechnology and pharmaceutical industry, in particular with active immunization employing as targets molecules related with angiogenesis.

The process of formation of new blood vessels from pre-existent ones is called angiogenesis. This event is widely regulated through the equilibrium of pro- and anti-angiogenic factors. Among the diseases in which the course has been related with the induction of pro-angiogenic factors and the formation of new blood vessels in anomalous form are: (a) cancer (both primary tumors and their metastases), (b) acute and chronic inflammatory processes such as asthma, respiratory distress, endometriosis, atherosclerosis, and tissular edema, (c) diseases of infectious origin as the Hepatitis, and Kaposi sarcoma, (d) autoimmune diseases as diabetes, psoriasis, rheumatoid arthritis, thyroiditis, and (e) other diseases and states as the diabetic and newborn retinopathies, organ transplant rejection, macular degeneration, neovascular glaucoma, hemangioma, and angiofibroma (Carmelliet P. y Jain R K. Nature 407:249, 2000; Kuwano M, et al. Intern Med 40:565, 2001). A potentially attractive therapeutic procedure for many of these cases could be based on the inhibition of the activity of the pro-angiogenic factors, that stimulate the anomalous formation of blood vessels, via their neutralization, or that of their receptors, or by eliminating the sources that produces them.

Vascular endothelium growth factors are a family of molecules that induce the formation of new vessels specifically and directly (Leung Science 246:1306, 1989; Klagsburn M, Annual Rev Physiol 33:217, 1991). This family includes the vascular permeability factor, also known as vascular endothelium growth factor VPF/VEGF (now denominated VEGF-A), the placenta growth factor PlGF, the platelet derived growth factors PDGF-A and PDGF-B, and other four new molecules structurally and functionally related to VEGF-A designated VEGF-B/VRF, VEGF-C/VRP, VEGD-D/FIGF, and VEGF-E. (Olofsson B et al. PNAS USA 13:2576, 1996; Joukov V et al. EMBO J 15:290, 1996; Yamada Y et al. Genomics 42:483, 1997; Ogawa S et al. J Biol Chem 273: 31273, 1998).

VEGF-A is a homodimeric glycoprotein formed by two 23-kDa subunits (Ferrara N, et al. Biochem Biophys Res Comun 165:198, 1989), of which five monomeric isoforms exist, derived from the differential splicing of the same RNA. These include two isoforms that remain attached to the cellular membrane (VEGF 189 and VEGF 206), and three of soluble nature (VEGF 121, VEGF 145, and VEGF 165). VEGF 165 is the most abundant isoform in mammal tissues, except for lung and heart, where VEGF 189 predominates (Neufeld G et al. Canc Met Rev 15:153, 1995), and in placenta, where VEGF 121 expression prevails (Shibuya M A et al. Adv Canc Res 67:281, 1995).

VEGF-A is the most studied and characterized protein of this family, and its alteration has been described in a larger number of diseases. Its over-expression is associated to tumors of different origin and localization, and their metastasis (Grunstein J et al. Cancer Res 59:1592, 1999), chronic inflammatory processes as ulcerative colitis and Crohn's disease (Kanazawa S, et al. Am J Gastroenterol 96:822, 2001), psoriasis (Detmar M, et al. J Exp Med 180:1141, 1994), respiratory distress (Thickett D R et al. Am J Respir Crit Care Med 164:1601, 2001), atherosclerosis (Celletti F L et al. Nat Med 7:425, 2001; Couffinhal T et al. Am J Pathol 150:1653, 1997), endometriosis (McLaren J. Hum Reprod Update 6:45, 200), asthma (Hoshino M, et al. J Allergy Clin Immunol 107:295, 2001), rheumatoid arthritis and osteoarthritis (Pufe T et al. J Rheumatol 28:1482, 2001), thyroiditis (Nagura S et al. Hum Pathol 32:10, 2001), diabetic and newborn retinopathies (Murata T et al. Lab Invest 74:819, 1996; Reynolds J D. Paediatr Drugs 3:263, 2001), macular degeneration and glaucoma (Wells J A et al. Br J Ophthalmol 80:363, 1996; Tripathi R C et al. Ophthalmology 105:232, 1998), tissular edema (Kaner R J et al Am J Respir Cell Mol Biol. 22:640 2000; Ferrara N Endocrinol Rev 13:18, 1992), obesity (Tonello C et al. FEBS Lett 442:167, 1999), hemangiomas (Wizigmann S y Plate K H Histol Histopathol 11:1049, 1996), in the synovial fluid of patients with inflammatory arthropathies (Bottomley M J et al Clin Exp Immunol 119:182, 2000), and associated to transplant rejection (Vasir B, et al. Transplantation 71:924, 2001). In the particular case of tumors, the cells expressing the three basic isoforms of VEGF-A: 121, 165, and 189, are the ones that grow faster in vivo; while in final stages most tumors limit expression to the VEGF 165 isoform, or, in its absence, to a combination of 121 and 189 that far from being additive, evidences a cooperation that strengthens the tumor vascular network (Grunstein J. Mol Cell Biol 20:7282, 2000).

PlGF, described in 1991, is not able to induce endothelial proliferation in its homodimeric form (Maglione D et al. Proc Natl Acad Sci USA 88:9267, 1991, DiSalvo J et al. J Biol Chem 270:7717, 1995). With PlGF up-regulation, and with it, of the signal transduced via VEGFR-1, the endothelial cells amplify their responses to VEGF during the change to the angiogenic phenotype associated to certain pathologies (Carmeliet P et al. Nat Med 7:575, 2001). PlGF expression has been related to the vascularization of human meningioma and glioma (Nomura M et al. J Neurooncol 40:123, 1998). This molecule forms heterodimers with VEGF 165, with pro-angiogenic activity, and their over-expression has been described in the conditioned media of some tumor cell lines (Cao Y et al. J Biol Chem 271:3154, 1996), and associated to the evolution of rheumatoid arthritis and to primary inflammatory arthropathies, in general (Bottomley M J et al. Clin Exp Immunol 119:182, 2000).

The over-expression of the rest of the members of the VEGF family, less studied, is also associated to a number of pathologies. VEGF-B has been related to breast, ovary, and kidney tumors, and to melanomas and fibrosarcomas (Sowter H M, et al. Lab. Invest. 77:607, 1997; Salven P Am. J. Pathol. 153:103, 1998, Gunningham S P et al. Cancer Res 61:3206, 2001). The differential expression of the VEGF-B 167 isoform in vitro has been reported in tumor cells of diverse origin (Li X, et al. Growth Factors 19:49, 2001). VEGF-C and VEGF-D are involved in the regulation of lymphatic vessels formation (Joukov V. et al EMBO J. 15: 290, 1996), and VEGF-C over-expression is associated to tissular edemas, to tumors of the breast, lung, head and neck, esophagus, and stomach, lymphomas, prostate cancer, and metastatic nodes (Kajita T, et al. Br J Cancer 85:255, 2001; Kitadi Y, et al Int J Cancer 93:662, 2001; Hashimoto I, et al. Br J Cancer 85:93, 2001; Kinoshita J, et al. Breast Cancer Res Treat 66:159, 2001; Ueda M, et al. Gynecol Oncol 82:162, 2001; Salven P Am. J. Pathol. 153:103, 1998; O-Charoenrat P et al. Cancer 92:556, 2001). In the case of VEGF-D, its over-expression by tumor cells is related to an in vivo increase of lymphatic vasculature in the tumors and the increase of metastasis in lymphatic nodes (Stacker S A, et al. Nat Med 7:186, 2001; Marconcini L et al. Proc Natl Acad Sci USA 96:9671, 1999).

The alterations on endothelial cell function induced by the molecules of the VEGF family are mediated by their binding to cell receptors of the type tyrosine kinase class 3, that so far include: VEGFR1 (Flt1), VEGFR2 (KDR/Flk1), and VEGFR3 (Flt4) (Kaipainen A J. Exp. Med. 178:2077, 1993). The N-terminal domain 2 has been identified as responsible of the binding to the ligands, favoring the phosphorilation of the cytoplasmatic domain and transduction of the signal (Davis-Smyth T et al EMBO 15:4919, 1996).

Ligands identified for VEGFR1 include VEGF-A, PlGF, and VEGF-B, in decreasing order of affinity (Shibuya M Int J Biochem Cell Biol 33: 409, 2001). In endothelial cells, this receptor captures the circulating VEGF (Gille H et al *EMBO J.* 19:4064, 2000). The binding of VEGF-A to the VEGFR1 expressed in cells of the hematopoyetic lineage affects significantly the activation of transcriptional factor NFκB in the precursors of dendritic cells, and in B and T lymphocytes. This last interaction is relevant in the in vivo establishment of an unfavorable immunologic balance, where dendritic cells maturation and the fraction of T lymphocytes are reduced, a phenomenon observed on immunosupressed patients and in particular, with cancer (Dikov M M et al Canc Res 61:2015, 2001; Gabrilovich D et al. Blood 92:4150, 1998). Over-expression of VEGFR1 has been related with psoriasis, endometrial cancer and hepatocellular carcinoma (Detmar M, et al. J Exp Med 180:1141, 1994; Ng I O Am J Clin Patol 116:838, 2001; Yokoyama Y et al Gynecol Oncol 77:413, 2000).

The VEGFR2 receptor (KDR/Flk1) mediates the biological effects of VEGF-A, and also binds VEGF-C and VEGF-D. This receptor is expressed differentially on activated endothelium and in some cell lines of tumor origin where it establishes autocrine pathways with the secreted VEGF. Apart from being involved in the already mentioned pathologies that are related with the over-expression of its ligands, the over-expression of VEGFR2 has been related with the progression of endometrial cancer (Giatromanolaki A et al, Cancer 92:2569, 2001), malignant mesothelioma (Strizzi L et al. J Pathol 193:468, 2001), astrocytic neoplasms (Carroll R S et al. Cancer 86:1335, 1999), primary breast cancer (Kranz A et al. Int J Cancer 84:293, 1999), intestinal type gastric cancer (Takahashi Y et al Clin Cancer Res 2:1679, 1996), multiform glioblastoma, anaplastic oligodendroglioma, and necrotic ependimoma (Chan A S et al. Am J Surg Pathol 22:816, 1998). Over-expressig of KDR has also been associated to the autosomic disease VHL and to hemangioblastoma (Wizigmann-Voos S et al Cancer Res 55:1358, 1995), to the progression of diabetic retinopathy (Ishibashi T. Jpn J Ophthalmol 44:323. 2000) and, in combination with Flt-1 over-expression, to the delayed-type hypersensitivity reactions (Brown L F et al J Immunol 154:2801, 1995).

Lymphangiogenesis mediated by VEGF-C and VEGF-D results from their binding to the FLT4 receptor or VEGFR3, expressed in the lymphatic endothelium. In some cases, even when over-expression of the ligands is not present, the over-expression of the receptor has been related to an adverse prognosis in the course of a group of pathologic entities, including: diabetic retinopathy (Smith G. Br J Ophthalmol 1999 April; 83(4):486-94), chronic inflammation and ulcers (Paavonen K et al, Am J Pathol 156:1499, 2000), the establishment of metastasis in lymphatic nodes and progression of breast cancer (Gunningham S P. Clin Cancer Res 6:4278, 2000 Valtola R et al. Am J Pathol 154:1381, 1999), associated to nasopharyngeal tumors and squamous oral carcinomas (Saaristo A et al. Am J Pathol 157:7, 2000; Moriyama M et al. Oral Oncol 33:369, 1997). Moreover, the over-expression of VEGFR3 is a sensitive marker of Kaposi sarcoma, type Dabska hemangioendothelioma and of cutaneous lymphangiomatosis (Folpe A L et al. Mod Pathol 13:180, 2000; Lymboussaki A et al. Am J Pathol 153:395, 1998).

Recently, two receptors were identified for VEGF named NRP1 and NRP2. These belong to the neurophilins family (NRP), and act as co-receptors for some specific isoforms of proteins of the VEGF family: VEGF-$A_{145}$ VEGF-$A_{165}$, VEGF-$B_{167}$ and PlGF1, increasing their mitogenic capacity. The expression of NRP1 has become a marker of the aggressiveness of prostate cancer, has been related to the increase of angiogenesis in melanomas, and with apoptosis escape events in breast cancer (Latil A et al. Int J Cancer 89:167, 2000; Lacal P M J Invest Dermatol 115:1000, 2000; Bachelder R E Cancer Res 61:5736, 2001). The coordinate over-expression of NRP1, KDR, and VEGF-$A_{165}$ have been related to the fibrovascular proliferation in diabetic retinopathy cases and rheumatoid arthritis (Ishida S. et al. Invest Ophthalmol V is Sci 41: 1649, 2000; Ikeda M. Et al. J Pathol 191:426, 2000). NRP2 is over-expressed in osteosarcomas where it promotes angiogenesis and tumor growth (Handa A et al. Int J Oncol 17:291, 2000).

Most of the therapeutic strategies based on angiogenesis inhibition, especially in cancer treatment, are based in the blockade of molecules of the VEGF family and their receptors, with clinical trials in course using: (1) monoclonal antibodies blocking VEGF or the KDR receptor, (2) metalloproteinase inhibitors, as Neovastat and Prinomastat, (3) VEGF inhibitors as Thalidomide, Suramin, Troponin I, and IFN-α and Neovastat, (4) blockers of VEGF receptors as SU5416, FTK787 and SU6668, (5) inducers of tumor endothelium apoptosis, as Endostatin and CA4-P, and (6) ribozymes that decrease VEGF or VEGF receptors expression (Angiozyme). Due to the high homology between human VEGF and its receptors KDR and Flt-1 with their murine homologs (~90%, 81%, and 89%, respectively), many animal models are used routinely to evaluate the preclinical effectiveness of antiangiogenic compounds directed to this system (Hicklin D J et al. DDT 6:517, 2001).

Passive administration of antibodies to VEGF or VEGFRs is successfully tested in different clinical phases in humans (Hicklin D J et al. DDT 6:517, 2001). The anti-VEGF humanized monoclonal antibody A.4.6.1 (Genentech, San Francisco, United States) is in phase III clinical trial for the treatment of colon, breast, kidney, and lung tumors (Kim, K J et al. Nature 362:841, 1993; Boersig C. R&D Directions October 7:44, 2001). In particular, for the case of the KDR receptor, a monoclonal antibody has been developed (IMC-1C11, ImClone) that recognizes the N-terminal extracellular domain of this receptor, and inhibits proliferation and migration of leukemic human cells, increasing survival of xenotransplanted mice. At present, its effect is being studied in patients with colon cancer metastasis (Dias S et al. J Clin Invest 106:511, 2000). In the aforementioned trials, the absence of concomitant adverse effects with the application of these monoclonal antibodies has been demonstrated.

Notwithstanding the previous, a therapeutic modality not yet employed for the blockade of neoangionegesis is specific active immunotherapy (SAI). In the SAI of cancer, antigens as peptides, proteins or DNA are employed, mixed with appropriate adjuvants. SAI procedures pursue the stimulation of an immune response, both of the humoral (activation of B-lymphocytes), and cellular types (activation of T helper, and cytotoxic lymphocytes, and natural killer cells), associated to dendritic cell function as professional presenting cells in the MCHI and MHC II contexts (Bystryn J C, Medscape Hematology-Oncology 4:1, 2001; Parker, K C et al., J. Immunol 152:163, 1994; Nestle F O et al., Nature Medicine 7:761, 2001; Timmerman J M, Annual Review Medicine 50:507, 1999).

SAI is a rapidly growing field of experimental and clinical research, with attractive applications, especially in oncology, where more than 60 undergoing clinical trials based in procedures of SAI are reported, which surpass at present the clinical trials based on the use of monoclonal antibodies. In the particular case of cancer, the antigens used as immunogens for SAI are selected because of their physiological relevance and difficulty of being substituted in the processes of tumor phenotypic drift (Bodey B et al., Anticancer Research 20: 2665, 2000), and because of their high specific association with the growth and evolution of tumor tissues.

The strategy of treating cancer using SAI also considers preferably the identification of antigens expressed in different tumor types, what could increase the number of indications for the same vaccine preparation. Examples of these are carcinoembryonic antigen (CEA), HER2-neu, human telomerase, and gangliosides (Greener M., Mol Med Today 6:257 2000; Rice J, et al. J Immunol 167:1558, 2001; Carr A et al, Melanoma Res 11:219, 2001; Murray J L, et al. Semin Oncol 27:71, 2000).

In human tumors, VEGF is over-expressed in the tumor compartment (Ferrara, N. Curr. Top. Microbiol. Immunol. 237:1, 1999), and high levels of VEGF and its receptors have been demonstrated in the tumor-associated vasculature (Brekken R A. J Control Release 74:173, 2001). The stromal cells also produce VEGF in response to the stimulus of transformed cells, with the result that when tumor cells are removed, VEGF levels persist in the patients. The presence of VEGF and its receptors have a practical value for the establishment of prognosis and staging in cases of prostate, cervix, and breast tumors (George D J et al. Clin Cancer Res 7:1932, 2001; Dobbs S P et al. Br J Cancer 76:1410, 1997; Callagy G et al. Appl Immunohistochem Mol Morphol 8:104, 2000). On the other hand, VEGF is also within the group of soluble factors that, together with other cytokines like IL-10, TNF-α and TGF-β, (Ohm J E y Carbone D P, Immunol Res 23:263, 2001), could be implicated in the immunosuppression that characterizes cancer patients (Staveley K, et al. Proc Natl Acad Sci USA 95:1178, 1998; Lee K H, et al. J Immunol 161:4183, 1998). This immunosuppressive effect seems to be related to its binding to the Flt1 receptor (Gabrilovich D et al. Blood 92:4150, 1998).

The present invention describes procedures of SAI in experimental tumors using molecules of the VEGF family and their receptors. The antitumoral effects obtained could be based in at least four different mechanisms, without discarding their possible combinations: (a) direct destruction of cancer and stromal cells producing VEGF, by cytotoxic lymphocytes, (b) damaging of endothelial cells of tumor-associated vessels due to the capture or neutralization of the circulating VEGF via antibodies, (c) direct destruction of endothelial cells that express VEGF receptors, by cytotoxic lymphocytes or complement fixing antibodies, (d) activation of a local immune response as a consequence of the capture or neutralization of circulating VEGF, and its consequent elimination of its immunosuppressive effects.

Ideally, these treatments could be used to diminish or avoid the appearance of metastasis, to reduce or eliminate primary tumors as a first or second line therapy, in combination or not with other anti-tumor agents.

Active immunization directed to VEGF family and their receptors could also be efficient in the single or combined therapy of acute and chronic inflammatory processes (asthma, respiratory distress, endometriosis, atherosclerosis, tissular edema), infectious diseases (Hepatitis, Kaposi sarcoma), autoimmune diseases (diabetes, psoriasis, rheumatoid arthritis, thyroiditis, synovitis), diabetic and newborn retinopathies, organ transplant rejection, macular degeneration, neovascular glaucoma, hemangioma, and angiofibroma, among others.

DETAIL DESCRIPTION OF THE INVENTION

According to the present invention, the in vivo administration of oligonucleotide sequences encoding for proteins of the VEGF family, their receptors, co-receptors or their fragments, as well as of their polypeptidic variants, induces a cellular and humoral immune response with antiangiogenic and antitumoral effect.

Immunogens of polypeptidic nature of interest for the present invention, as well as their fragments, can be isolated from their natural sources or obtained by synthesis or recombinant DNA technology. These polypeptides can also be produced fused to proteins having known adjuvant activity, such as p64K, (R. Silva et al U.S. Pat. No. 5,286,484 and EP 0474313), or covalently bound to adjuvants following the polypeptide synthesis. Other available strategies in these cases is are the obtainment of the natural polypeptide, its mutated or modified variants, and their fragments, as a part of loops exposed or not in bacterial proteins like OMP1, which are part of immunostimulatory preparations, in this particular case VSSP (R. Perez et al U.S. Pat. Nos. 5,788,985 and 6,149,921). Furthermore, it is possible to obtain the polypeptidic immunogen exposed in the surface of a viral particle (HbsAg, VP2 of parvovirus, etc.), bound to specific peptides that target cells or organs specialized in the induction of the immune response (CTLA4, Fc segment of the Ig, etc.), or to proteins capable of increasing biodistribution like VP22.

The principal natural sources of the proteins of interest for the present invention are predominantly expressed in placenta, activated endothelial cells, and tumor cells. The mRNA of these cells or tissues is used to obtain complementary DNA (cDNA) by known methods. The extracted RNA is used as template for the amplification through the polymerase chain reaction (PCR) of the cDNA corresponding to the selected antigen. In each case, primers used are designed according to the characteristics of the vector where the cDNA is going to be inserted and to the previously reported sequences of the protein of interest. Alternatively, and preferably in the case of the receptors amplified by PCR, that are the largest size antigens that are used in the present invention, the coding regions are amplified in two or more overlapping fragments. These fragments include a common ligation site used to assemble the intact DNA, starting with its fragments.

An alternative for the cloning of the antigens of interest is the selection from commercially available DNA libraries derived from human endothelium, or from tumors of this same origin. In some cases, it might be desirable to mutate some of the antigens object of the present invention, in order to avoid, especially with the VEGF family, an angiogenesis induction event produced by vaccination. These mutations are made preferably in the receptor binding sites already described in the literature. For this, primers are designed that cover both ends of the desired molecule, and the PCR products are used as template to obtain the mutated molecule. These mutated variants lack biological activity but reproduce the immunogenic properties of the selected antigen.

The cDNA molecules obtained by the methods described earlier are administered in a proper vector, being this a virus, a plasmid, a bacterial artificial chromosome, or similar. The vector carries the elements needed for the adequate expression of the gene in target cells, as well as the rest of elements that allows it to be produced in the host cellular system according to its nature. DNA molecules of the present invention might contain one or more genes of interest, constituted by one or more nucleic acids (cDNA, gDNA, synthetic or semi-synthetic DNA, or similar) that when transcribed or translated (when appropriate) in target cells generates the products with therapeutic/vaccine value.

Generally, the gene of the vaccine therapeutic product according to the invention is under the control of a transcriptional promoter that is functional in the target cell or the organism (mammals), as well as of a 3' end region that contains the signals needed for termination and polyadenilation of the mRNA of the product of interest, allowing its expression. The promoter can be the natural promoter of the gene or a heterologous promoter transcriptionally active in the target cell. The promoter can be from eukaryotic or viral origin. Among eukaryotic promoters, it is possible to use any promoter or derived sequence that stimulates or represses the gene transcription, specifically or not, inducible or not, in a strong or weak manner. Additionally, the promoter region can be modified by the insertion of activators or inductor sequences, allowing the tissue-specific or predominant expression of the gene in question.

Besides, the gene of interest can contain a signal sequence for subcellular localization, in a way that its cellular localization or secretion could be modified in the cell where it is expressed, or elsewhere, once synthesized. It can also contain a sequence encoding for a region of specific binding to a ligand specific of immune tissue, being directed to the site where the response is generated, with the obtainment of the therapeutic/vaccine effect.

Additionally, the gene of interest can be preceded by the coding sequence for the mRNA replication machinery, in a way that mRNA is amplified in the target cell, increasing the expression of said gene, and with it, of the therapeutic/vaccine effect according to the invention. The replication machinery in question could be of alphavirus origin (Schlesinger S., Expert Opin Biol Ther. 1:177, 2001), more specifically derived from the Sindbis or Semliki viruses, or similar. In this particular case, the gene of interest is under the transcriptional control of a subgenomic promoter that allows the amplification of its mRNA in target cells, once the molecules according to the present invention have been internalized. Furthermore, the DNA vector might contain sequences that permit the replication of the molecules which are objects of the present invention, in mammalian cells. This allows an increase in the expression levels and/or of the therapeutic/vaccine effect (Collings A., Vaccine 18: 4601, 1999)

The DNA vector can be purified using standard techniques for plasmid DNA purification. These techniques include the method of purification by cesium chloride density gradient, in the presence of ethidium bromide, or alternatively, the use of ionic exchange columns or any other exchanger or method to separate DNA molecules (Ferreira G N, et al, Trends Biotechnol. 18:380, 2000).

The present invention includes the use of plasmidic DNA vectors, preferably those of the PAEC family of compact vectors for DNA immunization and gene therapy in humans (Herrera et al, Biochem. Biophys. Res. Commu. 279: 548, 2000). This family comprises vectors pAEC-K6 (Access number AJ278712), pAEC-M7 (Access number AJ278713), pAEC-42 (Access number AJ278714), pAEC-SPE (Access number AJ278715) and pAEC-SPT (Access number AJ278716). These vectors contain only the essential elements for the expression of the product of interest in mammalian cells, including human cells, and a replication unit in *Escherichia coli*. The transcriptional unit is formed by the immediate early promoter of human cytomegalovirus (CMV), a versatile multicloning site for the insertion of the product of interest, and the sequences for transcriptional termination and polyadenilation derived from simian virus 40 (SV40). In the replication unit, the vector contains the gene for kanamycin resistance (Tn903), and a pUC19 replication origin (ColE1), in order to guarantee a high copy number and the selection of the bacteria that bear the plasmid of interest.

Furthermore, the present invention includes the use of plasmidic DNA vectors, preferably those of the PMAE family of compact vectors for DNA immunization in humans. These contain the same functional elements in bacteria as PAEC series, as well as the CMV immediate early promoter and the multicloning site. Additionally, they bear a synthetic intron and a synthetic sequence for transcription termination and polyadenilation, derived from rabbit β-globin. It has been reported that with sequences similar to the latter it is possible to obtain higher expression levels of the cloned gene (Norman J A et al, Vaccine 15: 801, 1997). Moreover, the vectors of this series include consecutive repetitions of immunostimulatory sequences (CpG motives), that stimulate innate immune system in both mice and humans, with the consequent activation of a humoral and cellular response against the molecule of interest (Krieg A M, Vaccine 19:618, 2001).

The immunization with recombinant virus (adenovirus, adeno-associated, vaccinia, chickenpox virus, canarypox virus, among others) produces a potent cytotoxic cellular response in the hosts. To introduce the sequence of interest in the recombinant virus vectors that have integration sequences and promoters that are particular for each virus type, are used. This strategy is also included in the scope of the present invention, and chickenpox virus and the pFP67xgpt vector are preferably used. The pFP67xgpt vector is used to clone genes under a strong early/late promoter of synthetic nature between the open reading frames 6 and 7 of a fragment of 11.2 kB BamHI of the chickenpox virus FP9. This plasmid also contains the Ecogpt controlled by the vaccinia promoter p7.5K, which is used to identify recombinant virus.

Other alternative of the present invention consists of the immunization with proteins of the VEGF family and their receptors and/or co-receptors. cDNA molecules obtained as previously described are cloned in vectors for expression in virus, yeast, phage, plants, or superior cells, in order to obtain the protein variants of the antigens, after their sequence has been verified by the traditional methods of automatic sequencing. Several vectors for expression have been described and used for the obtainment of recombinant proteins. These vectors contain, at least, a sequence that controls the expression operatively linked to the sequence of the DNA or fragment to be expressed. Examples of sequences useful for the control of expression are: the systems lac, trp, tac, and trc, the promoter regions and the principal operator of lambda phage, the controller region of the surface protein fd, the glycolytic promoters of yeast (for example, the 3-phosphoglicerate kinase), the promoters of yeast acid phosphatase (for example, Pho5), the yeast promoters for the mating alpha factor, and the promoters derived from polyoma, adenovirus, retrovirus, simian virus (for example, the early/late promoters of SV40), and other known sequences that regulate the expression of genes in prokaryotic and eukaryotic cells, their viruses, and their combinations.

The hosts used for the replication of these vectors and the obtainment of the recombinant proteins object of the present invention include prokaryotic and eukaryotic cells. The prokaryotic comprise *E. coli* (DHI, MRC1, HB101, W3110, SG-936, X1776, X2282, DH5a), *Pseudomonas, Bacillus subtilis, Streptomices*, and others. The eukaryotic cells include yeast and fungi, insects, animal cells (for example, COS-7 and CHO), human, and plant cells, and tissue cultures, among others. After the expression in the system of choice in an adequate media, the polypeptides or peptides can be isolated by known procedures.

Use of Adjuvants

Even when vaccination with naked DNA or proteins has shown to be effective in certain animal models, the patients affected by tumors or autoimmune diseases present a challenge to the therapeutic strategy proposed by the present invention. To favor the immune response, the DNA or protein vaccines can be combined with immunopotentiators already described like: mineral salts (ex., Aluminum hydroxide, aluminum phosphate, calcium phosphate); immunoestimulators like: cytokines (ex., IL-2, IL-12, GM-CSF, IFN-α, IFN-γ, IL-18), molecules (ex., CD40, CD154, invariant chain of MHC type I, LFA3); saponins (ex., QS21), MDP derivatives, CpG oligos, LPS, MPL and polyphosphazenes; lipidic particles like: emulsions (ex., Freund, SAF, MF59), liposomes, virosomes, iscoms, co-chelators; microparticular adjuvants like PLG microparticles, poloxamers, of viral type (ex., HBcAg, HCcAg, HBsAg), and of bacterial type (ie., VSSP, OPC); and mucosal adjuvants like heat-labile enterotoxin (LT), cholera toxin, and mutant toxins (ex., LTK63 y LTR72), microparticles and polymerized liposomes. In the case of DNA vaccination, the expression of the antigen of interest could be combined with some of the immunopotentiator molecules already mentioned, on a bi-cistronic vector.

The experimental situations detailed in the examples demonstrate that DNA can be coupled in a non-covalent manner to some of the mentioned particles and that the use of these mixtures reduce the optimal concentration to obtain an anti-tumor response, similar to those described for higher doses of naked DNA.

Administration to a Mammal

For the therapeutic applications, the vaccine preparations of the present invention are administered to a mammal, preferably a human, in a dose pharmaceutically acceptable, by the following routes: mucosal, subcutaneous, intramuscular, peritoneal, intra-lymphatic, topic, and by inhalation, among others. These could be administered on the tissue interstitial space, including: muscle, skin, brain, lung, liver, bone marrow, spleen, thymus, heart, lymph nodes, blood, bone, cartilage, pancreas, kidney, bladder, stomach, intestine, testicles, ovary, uterus, rectum, eye, glands, and connective tissue. In the case of vectors for oligonucleotide transfer, their expression is preferably directed to somatic differentiated cells, though they may be directed to non-differentiated or less differentiated cells like skin fibroblasts and blood pluripotent cells.

The doses of the immunogen could be administered in pharmaceutically accepted vehicles without toxicity or therapeutic effects. Examples of these vehicles include: ionic exchangers, alumina, aluminum esthearates, lecitine, seric proteins like albumin, buffer solutions, like phosphates, glycine, sorbic acid, potassium sorbate, partial glyceride mixtures of saturated fatty acids of plant origin, water, salts, or electrolites, like protamine sulphate, di-sodic hydrogen phosphate, sodium chloride, zinc salts, colloidal silica, magnesium trisilicate, polivynil pirrolidone, substances base on cellulose and polyethylene glycol. In the present invention, preferably phosphate buffers as vehicles of the vaccine preparations are used.

In the case of the use of proteins and peptides, these can be conjugated in covalent or non-covalent manner to molecules known as carriers that act like adjuvants. Among these molecules are: KLH, p64K, OPC (Musacchio A et al, Vaccine 19; 3692, 2001), and VSSP. The combination of naked DNA, viral vectors, and protein immunogens is an alternative also included within the scope of the present invention.

In an advantageous manner, plasmid DNA administration allows the generation of formulations with one or more molecules of interest in the vaccine preparation. Thus, molecules according to the present invention can be administered in vaccine schedules through the combination of different types of vectors (variant of induction re-stimulation, with DNA, proteins, viral vectors)

DNA vectors could be directly administered to the patient, or host cells can be in vivo or ex vivo modified with these vectors. This last strategy can be combined with the insertion by site-specific recombination or the immunization by somatic transgenesis that directs the vector expression to specific cells. Furthermore, bacterial hosts of DNA vectors could be used as their vehicles of transfer in vivo.

In this way, the molecules carrying the genes according to the present invention could be used in the form of naked DNA, or in combination with different vectors: chemical/ biochemical/biologic, natural/synthetic or recombinant. These molecules can be coupled or combined with cationic peptides, compacting molecules (ex. PEG, PEI), nuclear localization peptides (NLP), etc. These could be administered also together with cations capable of forming DNA precipitates, as a part of liposomal preparations to which the molecules have been added previously to the membrane fusion, and in synthetic vectors of lipid nature, or formed by cationic polymers (ex. DOGS or DOTMA). For the administration of the DNA vectors, chimeric proteins able to compact DNA and mediate the transport of the complex formed, and its selective endocytosis by specific cells, can also be used. DNA molecules carrying the therapeutic/vaccine genes according to the invention could be used for the genetic transfer to cells using physical methods of transfer, like particles bombardment, electroporation (in vitro, in vivo or ex vivo), or directly in vivo by topic application, inhalation by particulation, etc. The live vectors include adenoviral particles or the same hosts where the molecules according to the present invention have been generated.

The doses of polypeptides and/or oligonucleotides to be used can be established according to different parameters, in particular depending on the gene or protein administered as an immunogen, the route of administration, the pathology to be treated, the period of treatment, and in the case of using oligonucleotides, of the vector used for immunization. A change in dose schedule or administration route different to those described in the following examples, do not separate from the principle or precept of the present invention, being possible to achieve an optimization of the immunization schemes to obtain a better response.

Therapeutic Uses

The present invention has advantages over passive immunotherapy, which is in advanced phases of clinical trials using the same molecules as targets. In comparison with passive transfer of immunity through the administration of monoclonal antibodies (ex. Anti-VEGF), the immunization, be it with the protein or the oligonucleotide, has the advantage of inducing the endogenous production of antibodies and in addition the proliferation and expansion of specific cytotoxic CD8+ lymphocytes.

The present invention has advantages over the therapeutic strategies directed to block VEGF-VEGFRs system, mainly because these strategies only diminish the levels of circulating VEGF or block KDR. The strategy proposed, apart from achieving the mentioned effects, also destroys the source of VEGF (that is, the tumor cells and associated stroma) and/or the cells expressing their receptors (tumor endothelium and some tumor cells). Previous work done in this area only describe a humoral response as a principal component of the observed effect. Without the intention of limiting the scope of the present invention to a particular mechanism, the examples show that, besides from the humoral specific response, the vaccine compositions are able to elicit a CD8+ cellular response that cooperates with the humoral response; and that in the tumor context, the combination of both are relevant to obtain an anti-tumor effect, the previous observed in example 9.

It is possible that the cytotoxic cellular response is mediated by the recognition of some of the peptides that appear in Tables 1 and 2. In these, some peptidic segments appear, that could be relevant in the cellular response directed to selected targets in VEGF family, its receptors and co-receptors. This information was obtained through computer analyses on public databases from NIH and Heidelberg Institute using BIMAS and SYFPHEITI software, respectively. The peptides marked and other sequences derived from the antigens of interest could be used for the active immunotherapy of the already described pathologies, as a single or combined treatment, and as part or not of molecules with adjuvant capacities. These peptides can also be used in their oligonucleotide variants with vaccine purposes.

The methods to inhibit angiogenesis and the pathologic conditions associated to this event, comprise the administration of an effective amount of the DNA or protein of some of the molecules described in this invention, by any of the routes, and with the use of some of the previously described immunopotentiators or adjuvants, to a mammal. This mammal is preferably a human.

A non-reversible and unregulated increase of angiogenesis has been related to a wide group of diseases. The system that comprises the VEGF family, its receptors and co-receptors is over-expressed in many of these pathological conditions, as it has been described before. In this way, the therapeutic strategies proposed by the present invention result effective in the treatment of: (a) cancer (both primary tumors and their metastasis), (b) acute and chronic inflammatory processes like asthma, respiratory distress, endometriosis, atherosclerosis, and tissular edema, (c) diseases of infectious origin like Hepatitis and Kaposi sarcoma, (d) autoimmune diseases like diabetes, psoriasis, rheumatoid arthritis, thyroiditis, and (e) other diseases and states such as diabetic and newborn retinopathies, organ transplant rejection, macular degeneration, neovascular glaucoma, hemangioma and angiofibroma.

Particularly in the case of cancer, vaccination with the immunogens proposed by the present invention results effective in the treatment of carcinomas, sarcomas and vascularized tumors. Some examples of tumors that can be treated with the proposed strategies include epidermoid tumors, squamous tumors like those of the head and neck, and colorectal, prostate, breast, lung (including small and non-small cells), pancreas, thyroid, ovary, and liver tumors. These methods are also effective in the treatment of other types of tumors, like Kaposi sarcoma, central nervous system neoplasia (neuroblastoma, capillary hemangioma, meningioma and brain metastasis), melanomas, renal and gastrointestinal carcinomas, rhabdomyosarcoma, glioblastoma and leiomiosarcoma.

Specifically the use of VEGF-A and/or their receptors VEGFR-1 and VEGFR-2 as immunogen is useful for the treatment of: tumors of different origins and localizations and their metastasis, of hemangioma, of endometriosis, of tissue edemas, of chronic inflammatory processes like ulcerative colitis and Crohn's disease, of, atherosclerosis, of rheumatoid arthritis and osteoarthritis, of inflammatory arthropathies, psoriasis, respiratory distress, asthma, thyroiditis, of diabetic and newborn retinopathies, macular degeneration, and glaucoma, of the autosomic VHL disease, of obesity, and of the rejection of some organ transplants. On the other hand, a response vs PlGF is useful in cases of rheumatoid arthritis and in general for the treatment of primary inflammatory arthropathies.

In the case of VEGF-B, its use as immunogen results useful in cases of breast, ovary, and kidney tumors, and for melanoma and fibrosarcoma. The use of VEGF-C and its receptor VEGFR-3 results useful in the treatment of tissular edema, diabetic retinopathy, chronic inflammation, ulcers, and tumors of the breast, lung, head and neck, esophagus, stomach, lymphomas, and prostate, metastatic nodules and Kaposi sarcoma, Dabska type hemangioendothelioma and of the cutaneous lymphangiomatosis. Immunization with VEGF-D can be used specifically for the treatment of lymphatic node metastasis.

The use of NRP1 and NRP2 co-receptors in mammal immunization results useful for the treatment, in particular, of fibrovascular proliferation in prostate cancer, melanoma, osteosarcoma, breast cancer metastasis, diabetic retinopathy, and rheumatoid arthritis.

The studies based on the passive immunotherapy by administration of antibodies have shown that the combination of antibodies vs VEGF-A and KDR is more effective in models of syngeneic tumors. Thus, the use of two or more of the immunogens proposed in the present invention provides an especially efficient treatment for the inhibition of angiogenesis and tumor growth. These immunogens can be administered in an individual manner or by pairs using bi-cistronic vectors by the already mentioned pathways. Furthermore, vaccine compositions of the invention can be used together with, or in sequential manner, with drugs or chemotherapeutic agents, that offer a benefit to the condition under treatment.

The results described below demonstrate that the antiangiogenic and anti-tumor responses are mediated by a cooperation of the humoral and cellular responses. In particular, VEGF and its receptor are involved in the process of maturation of dendritic cells and act on B and T lymphocytes precursors. Example 10 demonstrates that the proposed therapeutic strategy, apart from diminishing the levels of VEGF in sera also contributes to the normalization of the proportions of B and T lymphocytes, and of mature dendritic cells. This effect favors the presentation of tumor antigens within the MHC I context, improving the quality and intensity of the immune anti-tumor response directed not only to the immunogen, but also to the other tumor-associated, tumor-specific, and over-expressed antigens, in the tumor context.

TABLE 1

Estimation of the VEGF protein family MHCI associated peptides in the context of HLAA.0201

A.-Using BIMAS software

| SEQ ID | VEGF-A Secuencia | Kd | SEQ ID | VEGF-B Secuencia | Kd | SEQ ID | VEGF-C Secuencia | Kd | SEQ ID | VEGF-D Secuencia | Kd | SEQ ID | PlGF Secuencia | Kd |
|---|---|---|---|---|---|---|---|---|---|---|---|---|---|---|
| 27 | LLSWVHWSL | 272 | 37 | LLLAALLQL | 309 | 47 | YLSKTLFEI | 640 | 57 | FMMLYVQLV | 1966 | 67 | RLFPCFLQL | 150 |
| 28 | ALLLYLHHA | 42 | 38 | QLAPAQAPV | 70 | 48 | TLFEITVPL | 324 | 58 | KLWRCRLRL | 620 | 68 | VVSEYPSEV | 42 |
| 29 | WSLALLLYL | 30 | 39 | QLVPSCVTV | 70 | 49 | VLYPEYWKM | 304 | 59 | QLFEISVPL | 324 | 69 | VMRLFPCFL | 42 |
| 30 | FLQHNKCEC | 23 | 40 | LMGTVAKQL | 26 | 50 | CMNTSTSYL | 85 | 60 | YISKQLFEI | 88 | 70 | RALERLVDV | 34 |
| 31 | WVHWSLALL | 20 | 41 | LLAALLQLA | 19 | 51 | KLFPSQCGA | 64 | 61 | CMNTSTSYI | 41 | 71 | VELTFSQHV | 32 |
| 32 | FLLSWVHWS | 16 | 42 | LLQLAPAQA | 8 | 52 | LLGFFSVAC | 32 | 62 | VLQEENPLA | 35 | 72 | AVPPQQWAL | 14 |
| 33 | RQLELNERT | 6 | 43 | VVSWIDVYT | 6 | 53 | SLPATLPQC | 11 | 63 | WVVNVFMM | 27 | 73 | LQLLAGLAL | 14 |
| 34 | NITMQIMRI | 3 | 44 | CVPTGQHQV | 6 | 54 | GLQCMNTST | 7 | 64 | VNVFMMLYV | 10 | 74 | RSGDRPSYV | 10 |
| 35 | YCHPIETLV | 2 | 45 | KQLVPSCVT | 4 | 55 | AAFESGLDL | 4 | 65 | SLICMNTST | 7 | 75 | LLAGLALPA | 8 |
| 36 | IEYIFKPSC | 2 | 46 | VVVPLITVEL | 3 | 56 | EQLRSVSSV | 4 | 66 | CVLQEENPL | 7 | 76 | CVPVETANV | 6 |

B.-Using SYFPEITHI software

| SEQ ID | VEGF-A Secuencia | Score | SEQ ID | VEGF-B Secuencia | Score | SEQ ID | VEGF-C Secuencia | Score | SEQ ID | VEGF-D Secuencia | Score | SEQ ID | PlGF Secuencia | Score |
|---|---|---|---|---|---|---|---|---|---|---|---|---|---|---|
| 77 | LLSWVHWSL | 24 | 87 | LLLAALLQL | 29 | 97 | TLFEITVPL | 27 | 107 | FMMLYVQLV | 25 | 117 | ALERLVDVV | 26 |
| 78 | ALLLYLHHA | 24 | 88 | QLAPAQAPV | 26 | 98 | DLEEQLRSV | 26 | 108 | QLFEISVPL | 25 | 118 | RLFPCFLQL | 24 |
| 79 | WVHWSLALL | 20 | 89 | QLVPSCVTV | 26 | 99 | YLSKTLFEI | 26 | 109 | YISKQLFEI | 24 | 119 | RALERLVDV | 24 |
| 80 | SLALLLYLH | 20 | 90 | VVVPLITVEL | 24 | 100 | ALLPGPREA | 24 | 110 | KLWRCRLRL | 23 | 120 | LLAGLALPA | 22 |
| 81 | SYCHPIETL | 19 | 91 | LLRRLLLAA | 23 | 101 | CMNTSTSYL | 21 | 111 | RAASSLEEL | 22 | 121 | LAGLALPAV | 22 |
| 82 | NITMQIMRI | 19 | 92 | LLAALLQLA | 23 | 102 | DICGPNKEL | 21 | 112 | SLEELLRIT | 22 | 122 | VMRLFPCFL | 20 |
| 83 | FLLSWVHWS | 18 | 93 | FLRCQGRGL | 22 | 103 | AAAAFESGL | 20 | 113 | ATFYDIETL | 22 | 123 | CFLQLLAGL | 20 |
| 84 | WSLALLLYL | 18 | 94 | LTVELMGTV | 21 | 104 | AAFESGLDL | 20 | 114 | EISVPLTSV | 22 | 124 | QLLAGLALP | 20 |

TABLE 1-continued

Estimation of the VEGF protein family MHCI
associated peptides in the context of HLAA.0201

| 85 | HPIETLVDI | 18 | 95 | LRRLLLAAL | 20 | 105 | VLYPEYWKM | 20 | 115 | SLICMNTST | 20 | 125 | SAGNGSSEV | 20 |
| 86 | CNDEGLECV | 18 | 96 | LMGTVAKQL | 19 | 106 | IIRRSLPAT | 20 | 116 | VPLTSVPEL | 20 | 126 | VVSEYPSEV | 20 |

Note:
Values in bold correspond to those peptides or their regions, which coincide in both predictions.

TABLE 2

Estimation of VEGF family receptors MHCI associated peptides in the context of HLAA.0201

A.-Using BIMAS software

| VEGFR-1 | | | VEGFR-2 | | | VEGFR-3 | | | NRP-1 | | | NRP-2 | | |
|---|---|---|---|---|---|---|---|---|---|---|---|---|---|---|
| SEQ ID | Secuencia | Kd | SEQ ID | Secuencia | Kd | SEQ ID | Secuencia | Kd | SEQ ID | Secuencia | Kd | SEQ ID | Secuencia | Kd |
| 127 | FLYRDVTWI | 1942 | 137 | VLLWEIFSL | 1792 | 147 | VLLWEIFSL | 1793 | 157 | GLLRFVTAV | 2249 | 167 | WMYDHAKWL | 5121 |
| 128 | VLLWEIFSL | 1792 | 138 | SLQDQGDYV | 769 | 148 | RLLEEKSGV | 1055 | 158 | VLLGAVCGV | 1006 | 168 | ILQFLIFDL | 484 |
| 129 | KLLRGHTLV | 901 | 139 | VLLAVALWL | 739 | 149 | VLWPDGQEV | 981 | 159 | WMPENIRLV | 436 | 169 | YLQVDLRFL | 247 |
| 130 | GLLTCEATV | 257 | 140 | AMFFWLLLV | 427 | 150 | NLTDLLVNV | 656 | 160 | GILSMVFYT | 278 | 170 | ALYFSRHQV | 223 |
| 131 | TLFWLLLTL | 182 | 141 | VIAMFFWLL | 270 | 151 | KQAERGKWV | 557 | 161 | LLCAVLALV | 272 | 171 | NMLGMLSGL | 131 |
| 132 | ILLSENNVV | 179 | 142 | ILLSEKNVV | 179 | 152 | GVIAVFFWV | 369 | 162 | VLLHKSLKL | 134 | 172 | WLYTLDPIL | 129 |
| 133 | TLNLTIMNV | 160 | 143 | LLAVALWLC | 146 | 153 | KLVIQNANV | 243 | 163 | GMLGMVSGL | 131 | 173 | DIWDGIPHV | 56 |
| 134 | CVAATLFWL | 137 | 144 | KNLDTLWKL | 128 | 154 | ALWNSAAGL | 177 | 164 | FQLTGGTTV | 120 | 174 | KMEIILQFL | 44 |
| 135 | LLSIKQSNV | 118 | 145 | AVIAMFFWL | 113 | 155 | TLSLSIPRV | 160 | 165 | VLATEKPTV | 118 | 175 | VLNKLHAPL | 36 |
| 136 | SLQDSGTYA | 112 | 146 | LLLVIILRT | 108 | 156 | SQHDLGSYV | 159 | 166 | GPFLFIKFV | 81 | 176 | LLGATCAGL | 36 |

B.-Using SYFPEITHI software

| VEGFR-1 | | | VEGFR-2 | | | VEGFR-3 | | | NRP-1 | | | NRP-2 | | |
|---|---|---|---|---|---|---|---|---|---|---|---|---|---|---|
| SEQ ID | Secuencia | Score | SEQ ID | Secuencia | Score | SEQ ID | Secuencia | Score | SEQ ID | Secuencia | Score | SEQ ID | Secuencia | Score |
| 177 | TLFWLLLTL | 29 | 187 | VLLWEIFSL | 29 | 197 | VLLWEIFSL | 29 | 207 | VLLGAVCGV | 30 | 217 | NMLGMLSGL | 27 |
| 178 | VLLWEIFSL | 29 | 188 | LLVIILRTV | 28 | 198 | SIPGLNVTL | 27 | 208 | GLLRFVTAV | 29 | 218 | ILQFLIFDL | 26 |
| 179 | ILGPGSSTL | 28 | 189 | GLFCKTLTI | 26 | 199 | NLTDLLVNV | 27 | 209 | LLCAVLALV | 28 | 219 | DIWDGIPHV | 26 |
| 180 | LLCALLSCL | 27 | 190 | SIMYIVVVV | 27 | 200 | VLWPDGQEV | 26 | 210 | GMLGMVSGL | 28 | 220 | YLQVDLRFL | 26 |
| 181 | GLLTCEATV | 27 | 191 | IILVGTAVI | 26 | 201 | LLPRKSLEL | 26 | 211 | ALGVLLGAV | 28 | 221 | TLDPILITI | 26 |
| 182 | LLRGHTLVL | 27 | 192 | ALMSELKIL | 26 | 202 | ALWNSAAGL | 26 | 212 | VLLHKSLKL | 27 | 222 | ILAKPKMEI | 25 |
| 183 | ALMTELKIL | 26 | 193 | AASVGLPSV | 25 | 203 | IMDPGEVPL | 26 | 213 | VLATEKPTV | 26 | 223 | VLNKLHAPL | 25 |
| 184 | KLLRGHTLV | 25 | 194 | SISNLNVSL | 25 | 204 | RLWLCLGLL | 25 | 214 | QLTGGTTVL | 25 | 224 | LLGATCAGL | 25 |

TABLE 2-continued

Estimation of VEGF family receptors MHCI associated peptides in the context of HLAA.0201

| 185 | TLNLTIMNV | 25 | 195 | AMFFWLLLV | 25 | 205 | LIYFYVTTI | 25  | 215 | VLLGAVCGV | 30 | 225 | ALYFSRHQV | 23  |
| 186 | ILLSENNVV | 25 | 196 | ILLSEKNVV | 25 | 206 | LLEGQPVLL | 25  | 216 | GLLRFVTAV | 29 | 226 | GIGMRLEVL | 23  |

Note:
Values in bold correspond to those peptides or regions, which coincide in both predictions.

EXAMPLES

Example 1

Cloning and Transient Expression of Antigens

Human VEGF, its Isoforms and Functional Mutants

VEGF isoforms were cloned applying the polymerase chain reaction (PCR) using as template a cDNA obtained from a previous isolation of mRNA of CaSki cell line (ATCC CRL 1550), according to the manufacturer instructions (Perkin-Elmer), and utilizing primers SEQ ID NO: 1 and SEQ ID NO: 2. Bands corresponding to the amplification products of VEGF isoforms 121 SEQ ID NO: 19 and SEQ ID NO: 20, 165 and 189 were extracted from 2% agarose gels. After band digestion with endonucleases BamHI and EcoRI, the cDNAs from the VEGF isoforms were purified and cloned independently in the PAECΔ2 vector (proprietary vector of CIGB). Resulting plasmids were sequenced and determined to have no mutations with respect to the aminoacid sequences reported by the EMBL for the cloned isoforms. The cDNA corresponding to VEGF isoforms were subsequently cloned KpnI/EcoRV on the pMAE5Δ5 vector, that among other characteristics differs from pAECΔ2 by the presence of 5 immunostimulatory CpG sites.

cDNA from a VEGF variant deficient for the binding to the KDR receptor (VEGF$_{KDR(-)}$) was obtained by direct mutagenesis of the VEGF$_{121}$ isoform previously cloned, as described by Siemeister G et al (Siemeister G et al. J Biol Chem 273:11115, 1998).

The mutated variant SEQ ID NO: 21 and SEQ ID NO: 22 was generated by PCR using the following primers:
(A) Amplification of the 5' terminal fragment (315 bp): using primers with sequences SEQ ID NO: 3 and SEQ ID NO: 4.
(B) Amplification of the 3' terminal fragment (93 bp): using primers with sequences SEQ ID NO: 5 and SEQ ID NO: 6.

The fragments thus amplified were purified as referred, and were used in equimolar concentrations as a template for a fusion PCR using the primers corresponding to sequences SEQ ID NO: 7 and SEQ ID NO: 8. Resultant cDNA containing the mutation was digested BamHI/EcoRI, and was purified, and cloned in pAECΔ2 vector. The mutations introduced were checked by sequencing, and the DNA corresponding to VEGF$_{KDR(-)}$ was subcloned KpnI/EcoRV in pMAE5Δ5 vector resulting in pMAE5Δ5 VEGF$_{KDR(-)}$.

Plasmids used both in transfection and in animal vaccination were purified in endotoxin-free conditions, as described by Whalen R. et al. (Whalen R G y Davis H L. Clin Immunol Immunopathol 75:1, 1995). Briefly, DNA was purified using QIAGEN Endo-free systems following the manufacturer instructions, and the DNA was furthermore submitted to a second precipitation. Finally, DNA was dissolved in endotoxin-free PBS (SIGMA, USA) to a final concentration of 4 mg/mL.

1.2 Human VEGF Receptor (KDR/Flk1)

The cDNAs coding for the extracellular domain of KDR receptor of VEGF (KDR1-3) and for the transmembrane and intracellular domains of this receptor (KDR TC), were obtained from an RT-PCR using mRNA of the endothelial cell line HUVEC (Clonetic, USA), treated with human VEGF (Sigma) and Heparin (Sigma).

In the case of the extracellular domains 1 to 3 SEQ ID NO: 23 and SEQ ID NO: 24, the primers used correspond to sequences SEQ ID NO: 9 and SEQ ID NO: 10. After digestion of the amplified fragment (943 bp) with endonucleases BamHI and EcoRI, the cDNA coding for 1-3 domains of KDR was purified, and cloned in pAECΔ2 vector. Clones positive by restriction analysis were verified by sequencing of the corresponding DNA. The cDNA corresponding to KDR 1-3 was then subcloned KpnI/EcoRV in the already described pMAE5Δ5 vector (pMAE5Δ5 KDR1-3).

For the cloning of transmembrane and cytosolic regions of the receptor (SEQ ID NO: 25 and SEQ ID NO: 26) a two-step strategy was designed. For the insertion of the first segment, the primers corresponding to SEQ ID NO: 11 and SEQ ID NO: 12 were used. After the XbaI/BglII digestion of this 747 bp segment, the product was cloned in the pMAE5 vector, previously digested with the same enzymes, obtaining the plasmid PMAE5 KDR 747. This plasmid was digested BglII/NotI in order to insert the remaining carboxi-terminal fragment of 1091 by that was amplified using the primers corresponding to sequences SEQ ID NO: 13 and SEQ ID NO: 14. Clones positive by restriction analysis were verified by DNA sequencing and denominated pMAE5 KDR C.

1.2.1 Cloning of the Transmembrane and Cytosolic Regions of KDR in a Viral Vector For the cloning of transmembrane and cytosolic regions of VEGF receptor (KDR) on the chickenpox virus, the primers corresponding to sequences SEQ ID NO: 15 and SEQ ID NO: 16 were used. After digesting this 953 by segment with StuI/SmaI enzymes, the product was cloned in the pFP67xgpt vector, previously digested with the same enzymes. In this same vector, digested SmaI/BamHI, the remaining 919 by were inserted, that were amplified from the original cDNA using primers corresponding to sequences SEQ ID NO: 17 and SEQ ID NO: 18. Clones positive by restriction analysis were verified by DNA sequencing and denominated pFP67xgpt KDR C.

Chickenpox virus (FWPVs) were replicated in chicken embryo fibroblasts (CEF), in DMEM medium supplemented with 2% of fetal bovine serum (FBS). The pFP67xgpt KDR C was transfected using Lipofectin (Gibco BRL, Grand Island, USA) in CEF previously infected with the attenuated strain FP9. After 24 hours, fresh medium was added and cells were cultured for other 3 to 4 days. After this time, cells were frozen-thawed three times. Recombinant viruses expressing the gene coding for the Ecogpt enzyme were purified in selective media with mycophenolic acid (25 μg/mL), xantine (250 μg/mL), and hypoxantine (15 μg/mL) (MXH). The correct inclusion of the gene in recombinant viruses was checked by PCR. Recombinant viruses were denominated FPKDRgpt and non-recombinants used as negative control FP.

Example 2

In Vivo Expression of Antigens

In order to confirm the potential of the constructions made to express the proteins in vivo, these were injected in the femoral quadriceps muscle of C57BL6 mice (3 per group)

1. pMAE5Δ5-$VEGF_{121}$ (10 and 50 μg/mouse) in PBS pH 7.2
2. pMAE5Δ5-$VEGF_{165}$ (10 and 50 μg/mouse) in PBS pH 7.2
3. pMAE5Δ5-$VEGF_{189}$ (10 and 50 μg/mouse) in PBS pH 7.2
4. pMAE5Δ5-$VEGF_{KDR(-)}$ (10 and 50 μg/mouse) in PBS pH 7.2
5. pMAE5Δ5-KDR 1-3 (10 and 50 μg/mouse) in PBS pH 7.2
6. pMAE5 KDR C (10 and 50 μg/mouse) in PBS pH 7.2
7. FPKDRgpt ($2.5*10^7$ cfu) in PBS pH 7.2
8. PBS pH 7.2 (negative control)

48 hours after injection the animals were sacrificed and injected muscles extracted in one piece. A part of the muscular tissue was homogenized in presence of protease inhibitors and non-ionic detergents. Presence of VEGF in protein extracts was analyzed by Dot-Blot and by Western-Blot using a polyclonal antibody that recognizes all human VEGF isoforms (sc-152G), following described procedures. RNA was extracted from the remaining muscular tissue using TRI-Reagent (SIGMA). A total of 20 μg of RNA from each experimental situation were submitted to electrophoresis in 1% agarose gels containing formaldehyde. RNA was transferred to a nylon filter (HYBOND) and hybridized with the cDNA of VEGF 121 isoform labeled with $ATP^{32}$, that recognizes all VEGF isoforms, or with the cDNA of KDR similarly labeled. In both cases, filters were re-hybridized with the cDNA corresponding to a constitutive gene: the gliceraldehyde 3-phosphate deshydrogenase (GAPDH). In all the analyzed constructions bands corresponding to human VEGF and the cloned fragments of the KDR receptor were identified.

Example 3

In Vivo Protection Experiments Employing Vaccination with the Plasmid Containing the Gene Fragments of KDR, the VEGF Receptor Groups of 10 C57BL/6 mice were vaccinated or not with the following variants:
1. pMAE5Δ5-KDR 1-3 (1, 10, 50 and 100 μg/mouse) in PBS pH 7.2
2. pMAE5 KDR C (1, 10, 50 and 100 μg/mouse) in PBS pH 7.2
3. FPKDRgpt ($2.5*10^7$ cfu)
4. PBS pH 7.2 (negative control)
5. FP ($2.5*10^7$ cfu) (negative control group 3)

In every case, mice were immunized by intramuscular injection (im.) in the rear left foot with a total volume of 50 μl. All the animals were re-immunized 15 days later using the original immunization regime. The tumor challenge was developed thirty days after the last immunization, by a subcutaneous (sc.) injection of $10^4$ cells of B16-F10 melanoma (ATCC, CRL-6475) in the right ventral zone of every animal. Tumor growth was monitored with three weekly measurements until animals started to die.

In mice immunized with the pMAE5Δ5-KDR 1-3 plasmid a reduction of tumor size was evidenced at doses of 50 and 100 μg of DNA/mouse, significantly lower with respect to the negative control (Table 3). A survival analysis at day 33 revealed a significant increment (with respect to the negative control) of this parameter for the animals immunized with the said DNA doses of 50 and 100 μg per mouse, with respect to the un-immunized mice (group PBS pH7.2). In the case of pMAE5Δ5-KDR C (Table 3) a significant reduction of tumor volume was observed at the four doses used, with an increment in survival for doses from 100 to 10 μg/animal. The use of viral vectors reduced the volume and increased survival in the condition used for the FPKDRgpt construction (Table 3), in comparison to the respective negative control (group of mice immunized with the vector without insert FPgpt).

TABLE 3

Tumor volume and survival in mice immunized with the fragments of the VEGF receptor (KDR) gene.

| Group | [DNA μg] | Tumor Vol. (mm³) Day 24 | Survival (Day 43) |
|---|---|---|---|
| pMAE5Δ5-KDR 1-3 | 100 | 424.0 ± 199.2 (*) | (*) |
|  | 50 | 756.32 ± 435.9 (*) | () |
|  | 10 | 1024.2 ± 397.1 (*) | (ns) |
|  | 1 | 1334.2 ± 620.7 (ns) | (ns) |

TABLE 3-continued

Tumor volume and survival in mice immunized with the fragments of the VEGF receptor (KDR) gene.

| Group | [DNA μg] | Tumor Vol. (mm³) Day 24 | Survival (Day 43) |
|---|---|---|---|
| pMAE5Δ5-KDR C | 100 | 404.23 ± 200.0 (*) | (*) |
|  | 50 | 633.2 ± 365.2 (*) | (*) |
|  | 10 | 924.3 ± 437.1 (**) | (*) |
|  | 1 | 1114.2 ± 665.7 (*) | (ns) |
| FPKDRgpt | $2.5*10^7$ cfu | 304.23 ± 152.0 (*) | (*) |
| FPgpt | $2.5*10^7$ cfu | 1891.0 ± 726.0 (ns) | (ns) |
| PBS pH 7.2 | — | 1785.0 ± 826.0 | — |

Note
Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day.
Statistical signification is indicated as ns, $p \leq 0.05$ non-significant;
*, $p \leq 0.05$;
**, $p \leq 0.01$; and
***, $p \leq 0.001$.

Example 4

In Vivo Protection Experiments Using Vaccination with the Plasmids Containing the VEGF Isoforms, and the Mutated Variant Groups of 10 mice C57BL/6 were vaccinated or not with the following variants:
1. pAECΔ2-$VEGF_{121}$ (1, 10, 50 and 100 μg/mouse) in PBS pH 7.2
2. pMAE5Δ5-$VEGF_{121}$ (1, 10, 50 and 100 μg/mouse) in PBS pH 7.2
3. pMAE5Δ5-$VEGF_{165}$ (1, 10, 50 and 100 μg/mouse) in PBS pH 7.2
4. pMAE5Δ5-$VEGF_{189}$ (1, 10, 50 and 100 μg/mouse) in PBS pH 7.2
5. pMAE5Δ5 $VEGF_{KDR(-)}$ (1, 10, 50 and 100 μg/mouse) in PBS pH 7.2
6. PBS pH 7.2 (negative control)

In every case, mice were immunized by im. injection in the rear left foot with a total volume of 50 μl. All the animals were re-immunized 15 days later using the original immunization regime. The tumor challenge was developed thirty days after the last immunization, by a subcutaneous injection of $10^4$ cells of B16-F10 melanoma (ATCC, CRL-6475) in the right ventral zone of every animal. Tumor growth was monitored with three weekly measurements until animals started to die.

For the naked DNA variant in pAEC series in the case of mice immunized with 100 μg/animal, a decrease in tumor growth with respect to the negative control was observed (Table 4). In the variants included in the vector of the pMAE5Δ5 series with 5 CpG sites, independently of the VEGF isoform, tumor size was significantly reduced as compared to the negative control in the groups of mice immunized with doses of 10, 50, or 100 μg of DNA. In the case where the mutated variant pMAE5Δ5 $VEGF_{KDR(-)}$ was used, a significant reduction of tumor size was obtained at similar doses as those employed with the pMAE5Δ5-$VEGF_{121}$.

A survival analysis on day 43 evidenced a significant increase (with respect to the negative control) of the animals immunized with the variants pMAE5Δ5-$VEGF_{121}$, pMAE5Δ5-$VEGF_{165}$, pMAE5Δ5-$VEGF_{189}$, and pMAE5Δ5 $VEGF_{KDR(-)}$, at doses of 50 and 100 μg per animal (Table 4).

TABLE 4

Tumor volume and survival in mice immunized with different variants of naked DNA containing the different isoforms of the VEGF gene and a mutated variant.

| Group | [DNA µg] | Tumor Vol. (mm³) (Day 24) | Survival (Day 43) |
|---|---|---|---|
| PAECΔ2-VEGF$_{121}$ | 100 | 991.5 ± 354 (*) | ns |
|  | 50 | 1429.2 ± 396 (ns) | ns |
|  | 10 | 1506.6 ± 442 (ns) | ns |
|  | 1 | 1660.5 ± 456 (ns) | ns |
| PMAE5Δ5-VEGF$_{121}$ | 100 | 645.0 ± 215 (***) | *** |
|  | 50 | 850.1 ± 463 (***) | *** |
|  | 10 | 992.1 ± 410 (*) | ns |
|  | 1 | 1560.3 ± 598 (ns) | ns |
| PMAE5Δ5-VEGF$_{165}$ | 100 | 799.2 ± 335 (***) | *** |
|  | 50 | 916.6 ± 390 (**) | ** |
|  | 10 | 1000.5 ± 662 (*) | ns |
|  | 1 | 1845.3 ± 450(ns) | ns |
| PMAE5Δ5-VEGF$_{189}$ | 100 | 790.1 ± 235 (***) | *** |
|  | 50 | 996.5 ± 255 (*) | ** |
|  | 10 | 1050.2 ± 362 (*) | ns |
|  | 1 | 1670.2 ± 408(ns) | ns |
| pMAE5Δ5 VEGF$_{KDR}$ (—) | 100 | 550.1 ± 335 (***) | *** |
|  | 50 | 894.7 ± 408 (**) | *** |
|  | 10 | 991.8 ± 362 (*) | ns |
|  | 1 | 1489.3 ± 510 (ns) | ns |
| PBS pH 7.2 | 0 | 1673.9 ± 712 |  |

Note:
Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day.
Statistical signification is indicated as ns, $p \leq 0.05$ non-significant;
*, $p \leq 0.05$;
**, $p \leq 0.01$ and
***, $p \leq 0.001$.

Example 5

In Vivo Protection Experiments Through Immunization with pMAE5Δ5-VEGF$_{121}$ and pMAE5Δ5-KDR 1-3, in a Model of Collagen-Induced Arthritis Groups of 20 mice were vaccinated or not with the following variants:
1. pMAE5Δ5-VEGF$_{121}$ (50 µg of DNA/mouse) in PBS pH 7.2
2. pMAE5Δ5-KDR 1-3 (50 µg of DNA/mouse) in PBS pH 7.2
3. PBS pH 7.2 (Negative control)

In all cases immunization (day 0) was by im. route in the rear left foot with a total volume of 50 µl. All the animals were re-immunized 15 days later using the original immunization regime.

On day 5 the induction of autoimmune arthritis began by immunization with chicken collagen type II (Sigma), a model previously described by Campbell et al. (Campbell I K et al Eur. J. Immunol. 30: 1568, 2000). This immunization was repeated on day 26. The four extremities of each mouse were evaluated on a daily basis according to the arthritis index that establishes punctuation from 0 to 3 for each limb due to the presence in the examination of signs of erythema (1), inflammation (2), or articular rigidity (3), with a maximal value of 12. Mice started to show clinical symptoms of arthritis development 23 days after the induction, with the higher incidences at 50 days. Table 5 shows the analysis of arthritis incidence in the animals of the different experimental groups. In days 40 and 55 a significant reduction on arthritis incidence was observed in vaccinated groups (1 and 2) as compared to control group.

TABLE 5

Incidence of arthritis on selected days (40 and 55).

| Group | Incidence day 40 | Incidence day 55 |
|---|---|---|
| 1 | 20/8 (40%) | 20/9 (45%) |
| 2 | 20/6 (30%) | 20/12 (60%) |
| 3 | 20/10 (50%) | 20/14 (70%) |

Example 6

In Vivo Antiangiogenic Effect of Vaccination

Groups of 15 mice were vaccinated or not with the following variants:
1. pMAE5Δ5-VEGF$_{121}$ (50 µg of DNA/mouse) in PBS pH 7.2
2. pMAE5Δ5-KDR 1-3 (50 µg of DNA/mouse) in PBS pH 7.2
3. pMAE5 KDR C (50 µg/mouse) in PBS pH 7.2
4. PBS pH 7.2 (Negative control)

In every case, C57Bl/6 mice were immunized by im. injection in the rear left foot with a total volume of 50 µl. All the animals were re-immunized 15 days later using the original immunization regime. Thirty days after the last immunization, the in vivo angiogenesis was evaluated in the animals using matrigel as described by Coughlin M C et al. (Coughlin M C et al. J. Clin. Invest. 101:1441, 1998). The animals previously vaccinated were divided in groups of 5 and injected subcutaneously in the abdominal middle line with 500 µl of matrigel (Becton Dickinson and Co., Franklin Lakes, N.J., USA) containing:
1. VEGF 50 ng/mL, Heparin 50 U/mL
2. $10^5$ cells of B16-F10 melanoma
3. PBS Six days later the animals were sacrificed and the matrigel plug was extracted. Hemoglobin contents in the plugs were analyzed according to the manufacturer instructions (Drabkin's reagent kit; Sigma Diagnostics Co., St. Louis, Mo., USA).

Vaccination with the plasmids coding for VEGF or its receptor KDR inhibit significantly (p<0.001) the VEGF induced vascularization, as well as that induced by systems that are more complex: tumor cells.

Example 7

Obtainment of an Immunogen Based in the Non-Covalent Binding of pMAE5Δ5-VEGF$_{121}$ to Different Adjuvant Agents Different immunostimulatory agents, previously reported, were used, mixed with the pMAE5Δ5-VEGF$_{121}$ construction following with the methodology described below. The Opc protein from the outer membrane of Neisseria meningitidis was purified according to the report of Musacchio et al. (Musacchio A et al. Vaccine, 67:751, 1997). 50 µg/mL of pMAE5Δ5-VEGF$_{121}$ were added to 10 µg/mL of Opc with gentle shaking at acid pH. The resulting complex was extensively dialyzed overnight in endo-free PBS pH 7.2 (Sigma). The level of Opc protein-plasmid DNA association (Opc-pMAE5Δ5-VEGF$_{121}$) was checked by DNA visualization using 1% rose gel.

More than 50% of the plasmid DNA was associated to the Opc protein.

Very small particles (VSSP) coming from complex of outer membrane proteins (OMPC) of Neisseria meningitides, supplied by the Center of Molecular Immunology (R. Perez et al. U.S. Pat. Nos. 5,788,985, and 6,149,921), were used for combination with the plasmid DNA of interest. VSSP (1 mg) were incubated with 5 mg of pMAE5Δ5-VEGF$_{121}$ overnight with gentle agitation. The resulting material was extensively dialyzed in endo-free PBS pH 7.2 (Sigma). The level of VSSP-plasmid DNA association (VSSP-pMAE5Δ5-VEGF$_{121}$) was checked by DNA visualization using 1% agarose gel. More than 50% of the plasmid DNA was associated to the VSSP particles.

The Hepatitis C and Hepatitis B core particulated antigens (HCcAg and HBcAg) were produced according to a previous report (Lorenzo L J et al., Biochem Biophys Res Commun 281:962, 2001). One mg of the antigens were mixed with 5 mg of the plasmid in an overnight incubation. The levels of HCcAg or HBcAg-plasmid DNA association (HCcAg-pMAE5Δ5-VEGF$_{121}$ and HBcAg-pMAE5Δ5-VEGF$_{121}$, respectively) were checked by DNA visualization using 1% agarose gel. More than 50% of the DNA was associated to the antigenic particle, in each case.

Example 8

Experiments of In Vivo Protection with the pMAE5Δ5-VEGF$_{121}$ Construction and Immune Response Adjuvants Groups of 10 C57BL/6 mice were vaccinated or not with the following variants:
1. pMAE5Δ5-VEGF$_{121}$ (1, 10 and 50 μg of DNA/mouse) in PBS pH 7.2
2. Opc-pMAE5Δ5-VEGF$_{121}$ (1, 10 and 50 μg of DNA/mouse)
3. VSSP-pMAE5Δ5-VEGF$_{121}$ (1, 10 and 50 μg of DNA/mouse)
4. HBcAg-pMAE5Δ5-VEGF$_{121}$ (1, 10 and 50 μg of DNA/mouse)
5. HCcAg-pMAE5Δ5-VEGF$_{121}$ (1, 10 and 50 μg of DNA/mouse)
6. PBS pH 7.2 (Negative control for group 1)
7. Opc (Negative control for group 2)
8. VSSP (Negative control for group 3)
9. HBcAg (Negative control for group 4)
10. HCcAg (Negative control for group 5)

Immunization procedures, as well as tumor challenge and tumor volume measurements were similar to those described in the previous example. The vaccine variants with doses similar or higher to 10 μg of DNA/mouse decreased tumor growth in comparison to the respective negative controls (Table 6). A significant superior survival as compared to that of the respective control, was observed for the animals immunized with the VEGF gene, associated or not with Opc, VSSP, HCcAg and HBcAg, as immunopotentiator vehicles. All the variants with vehicle showed a significant superior survival versus the respective control, for doses starting with 10 μg/mouse, while the naked DNA variant with the vector pMAE5Δ5-VEGF$_{121}$ resulted significantly different from the negative control at the dose of 50 μg/mouse (Table 6).

TABLE 6

Tumor volume and survival of mice immunized using different immunostimulatory agents.

| Group | [DNA μg] | Tumor Vol. (mm$^3$). (Day 24) | Survival (Day 43) |
|---|---|---|---|
| pMAE5Δ5-VEGF | 50 | 1050.9 ± 689 (**) | ns |
|  | 10 | 1229.0 ± 596 (*) | ns |
|  | 1 | 1895.3 ± 596 (ns) | ns |
| OpC-pMAE5Δ5-VEGF | 50 | 960.6 ± 456 (**) | ** |
|  | 10 | 1100.5 ± 615 (**) | * |
|  | 1 | 1654.8 ± 663 (ns) | ns |
| VSSP-pMAE5Δ5-VEGF | 50 | 884.6 ± 410 (***) | ** |
|  | 10 | 1002.3 ± 598 (**) | * |
|  | 1 | 1532.7 ± 745 (ns) | ns |
| HBcAg-pMAE5Δ5-VEGF | 50 | 950.1 ± 570 (**) | ** |
|  | 10 | 1230.5 ± 662 (*) | * |
|  | 1 | 1867.2 ± 652 (ns) | ns |
| HCcAg-pMAE5Δ5-VEGF | 50 | 950.1 ± 570 (**) | ** |
|  | 10 | 1230.5 ± 662 (*) | * |
|  | 1 | 1867.2 ± 652 (ns) | ns |
| OpC (5 μg/mouse/dose) | 5 μg | 2059.0 ± 687 (ns) | ns |
| VSSP |  | 2156.0 ± 759 (ns) | ns |
| HBcAg (5 μg/mouse/dose) |  | 1998.2 ± 798 (ns) | ns |
| HCcAg (5 μg/mouse/dose) |  | 1897.0 ± 812 (ns) | ns |
| PBS pH 7.2 |  | 2073.0 ± 816 (ns) | ns |

Note:
Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day.
Statistical signification is indicated as ns, $p \leq 0.05$ non-significant;
*, $p \leq 0.05$;
**, $p \leq 0.01$; and
***, $p \leq 0.001$.

Example 9

In Vivo Protection Experiment Using VEGF in its Protein Form

Groups 10 C57BL/6 mice were vaccinated or not with the following variants:
VEGF165 (20 μg/mouse) with Complete and Incomplete Freund adjuvant
Complete and Incomplete Freund adjuvant (negative control)
VEGF$_{165}$ antigen was obtained from a commercial source (SIGMA) with more than 97% purity. Mice were immunized by the intraperitoneal route using Complete Freund's adjuvant (Sigma) with re-immunizations in days 15 and 30 by the same route but using Incomplete Freund's adjuvant. Tumor challenge, and measurements of tumor volume were similar to those described in the previous example.

A significant reduction in tumor volume and increase survival were observed in the VEGF immunized group as compared to the control non-immunized group. The effect was similar to those found in previous experiments using VEGF DNA.

Example 10

In Vivo Experiments of Immune Protection Transfer in C57BL/6 Mice with Severe Combined Immunodeficiency (SCID)

C57BL/6 mice were immunized or not with doses of 50 μg of pMAE5Δ5-VEGF$_{121}$ DNA/mouse using the procedures described in the example 5. Mice were sacrificed at 45 days after first immunization. CD8+, CD4+ and B-lymphocytes of these mice were separated using magnetic beads (Dynabeads, USA), according to the manufacturer instructions.

Groups of 10 six-week old C57BL/6 SCID mice were reconstituted with the following combinations of the previously extracted lymphocytes.

Group 1: CD8+ T-lymphocytes and CD4+ T-lymphocytes from mice immunized with pMAE5Δ5-VEGF$_{121}$ DNA. B-lymphocytes were not reconstituted.

Group 2: B-lymphocytes and CD4+ T-lymphocytes from immunized mice, and CD8+ T-lymphocytes from non-immunized mice.

Group 3: B-lymphocytes, CD8+ T-lymphocytes and CD4+ T-lymphocytes from immunized mice, as a positive control of the experiment.

Group 4: B-lymphocytes, CD8+ T-lymphocytes, and CD4+ T-lymphocytes from non-immunized mice, as a negative control of the experiment.

Reconstituted SCID mice were challenged sc. with $10^4$ B16-F10 melanoma cells. Tumor growth was monitored by three weekly measurements until mice start to die. Anti-VEGF antibody levels were analyzed through a laboratory ELISA. 96-well plates were incubated overnight with a 0.5 μg/ml solution of VEGF165 (Sigma). The wells were blocked with PBS-BSA 1% (BDH, UK) solution, and later incubated with serial dilutions of the animal sera. After washing with PBS-Tween 0.05%, a commercially available polyclonal anti mouse IgG (Sigma, A0168) was added. The signal was amplified in the presence of the commercial substrate ortho-phenilene-diamine (OPD, Sigma).

Table 7 reflects the results of tumor volume (Day 24) and survival (Day 40) of the groups of mice submitted to tumor challenge. Beginning on the day 15 after reconstitution, the animals of the groups 1 to 3 experienced a reduction in tumor size as compared to group 4, reconstituted with lymphocytes from non-immunized mice. Thus, the effect that provokes the immune system in the immunized mice, that allows the reduction in tumor size, is related to humoral and cellular responses, being the last one of the cytotoxic type (CTL), due to the absence of anti-VEGF antibodies in group 1. Nevertheless, in the experimental conditions used survival only increased in group 3 (B and T lymphocytes of immunized mice), as compared to the rest of the groups (Table 7). In the partially reconstituted animals where B or T of the CTL type responses were absent (groups 1 and 2, respectively) the survival was not different from the negative control. These results demonstrate that the combination of humoral and cellular responses (group 4), have a synergic effect that enables an effective response able to prolong the survival of mice submitted to the tumor challenge.

Example 11

Demonstration of Immunological Restoration by Depletion of Circulant VEGF Through Immune Response Groups of 15 C57BL/6 female mice were injected by im. route with the following variants:
1. pMAE5Δ5-VEGF$_{121}$ (50 μg/mouse) in PBS pH 7.2
2. PBS pH 7.2

In every case, mice were immunized by im. injection in the rear left foot with a total volume of 50 μl. All the animals were re-immunized 15 days later using the original immunization regime. Thirty days after the last immunization 5 randomly selected animals from each group were sacrificed to analyze the immunological state of the immunized and control animals, as well as the toxicity of vaccination on organs and tissues, through macroscopic and histological evaluations.

Remaining animals of each group received a sc injection of $10^4$ melanoma B16-F10 cells in the right ventral zone. At 15 and 30 days after tumor cells injection, 5 mice per group were sacrificed and evaluated as previously described.

Toxic events were not evidenced at macroscopic level in any of the evaluated animals, and histopathological analysis reveal no damage in any of the organs examined 30 days after the last immunization. Immunological evaluation consisted of: (1) evaluation of murine VEGF levels in serum; (2) cellular content of T and B lymphocytes, as well as the degree of maturity of dendritic cells in spleen, and in brachial axillary and inguinal lymph nodes.

The analysis of the levels of murine VEGF (R&D kit for murine VEGF) in the sera of un-treated animals showed that with the increase of time of exposure to tumor, the VEGF levels increased in serum, in concordance with the increase of tumor size with time. In the group immunized against human VEGF a significant reduction (p<0.001 ANOVA, post-test Bonferroni) of murine VEGF levels was detected, that lasted past 30 days after the tumor challenge.

The status of the immune system of the animals sacrificed on each moment was analyzed through the study of the proportions of the cellular populations present on lymph nodes and spleen, according to the reports of Gabrilovich et al. (Gabrilovich D et al. Blood 92:4150, 1998). For theses studies, commercial monoclonal antibodies that recognize CD3, CD19, CD11c and CD86 (B7-2) molecules (Pharmingen) labeled with fluorescein isothiocyanate (FITC) and phycoerythrine (PE), were used, that allowed the visualization of the cellular populations using a flow cytometer (FACS). Results obtained are shown in table 8.

TABLE 7

Tumor volume and survival in SCID mice reconstituted with lymphocytes from pMAE5Δ5-VEGF$_{121}$ immunized mice.

| | Mice donating lymphocytes to the C57BL/6 SCID | | | Tumor Vol. | Survival |
|---|---|---|---|---|---|
| Group | B Lymph. | CD4+ Lymph. | CD8+ Lymph. | (Day 24) | (Day 40) |
| 1 | — | immunized | immunized | 1067.8 ± 689 (ns) | ns |
| 2 | immunized | immunized | non immunized | 1129.0 ± 596 (ns) | ns |
| 3 | immunized | immunized | immunized | 652.3 ± 396 (***) | *** |
| 4 | Non immunized | Non immunized | Non immunized | 1856.0 ± 756 | — |

Note:
Donor mice were immunized or not with doses of 50 μg of pMAE5Δ5-VEGF DNA per mouse. Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day.
Statistical signification is indicated as ns,
$p \leq 0.05$ non-significant;
*, $p \leq 0.05$;
**, $p \leq 0.01$; and
***, $p \leq 0.001$.

TABLE 8

Summary of the results of FACS analysis of cell populations according to surface markers.

| | Total of Cells | | | | Fraction enriched with dendritic cells | |
| --- | --- | --- | --- | --- | --- | --- |
| | Lymph Nodes | | Spleen | | Lymph Nodes | Spleen |
| Group (day) | CD-19 | CD-3 | CD-19 | CD-3 | CD-11c/B7-2 | CD-11c/B7-2 |
| A. Non immunized | | | | | | |
| Non immunized (30 Days) | 8% | 86% | 38.1% | 40.8% | 60% | 62.4% |
| After tumor challenge (60 Days) | 20.1% | 60.5% | 3.8 | 11.4% | 32.8% | 10.2% |
| B. Immunized | | | | | | |
| Immunized (30 Days) | 7.2% | 87.3% | 40% | 39% | 58.6% | 60.3% |
| After tumor challenge (60 Days) | 10.9% | 80.1% | 25.4 | 34% | 53.5% | 52.9% |

Note:
In every case, values indicate the percent of positive cells from the total of quantified cells.

The analyses of lymphoid cell populations and of the maturation of dendritic cells in the animals, 30 days after the immunization, indicate that the vaccination with the VEGF DNA does not induce any change in the immune status of the animal. Nevertheless, 30 days after the tumor implantation, the non-vaccinated animals show a decrease in the T-lymphocyte/B-lymphocyte ratio (CD3/CD19) both in lymph nodes and in spleen, with respect to the ratio before the tumor challenge. Furthermore, in particular in the spleen, there is a significant reduction in the number of lymphoid cells. A reduction in the number of mature dendritic cells both in lymph nodes and in spleen was also observed in these animals. In the group of mice vaccinated with the VEGF DNA a significant recovery in all parameters was evidenced, that could be correlated with the reduction of the VEGF levels in the sera observed in the animals of this group.

INCORPORATION OF SEQUENCE LISTING

Incorporated herein by reference in its entirety is the Sequence Listing for the application. The Sequence Listing is disclosed on a computer-readable ASCII file titled, "SequenceListing976-19DIVII.txt", created on Nov. 4, 2009. The SequenceListing976-19DIVII.txt file is 58 kilobytes in size.

The invention claimed is:

1. An immunogenic composition comprising a vascular endothelial growth factor (VEGF) polypeptide impaired for receptor activation identified as the amino acid sequence set forth in SEQ ID NO: 21, and optionally further comprising a pharmaceutically acceptable adjuvant.

2. An immunogenic composition comprising an oligonucleotide encoding for a VEGF polypeptide impaired for receptor activation identified as the amino acid sequence set forth in SEQ ID NO: 21, and optionally further comprising a pharmaceutically acceptable adjuvant.

3. The immunogenic composition according to claim 1, wherein the adjuvant is selected from the group consisting of: recombinant particle of Hepatitis B Core Antigen, recombinant particle of Hepatitis C Core Antigen, OPC protein, KLH protein, Freund adjuvant, *Neisseria meningitides* p64k protein, and *Neisseria meningitides* outer membrane derived VSSP.

4. The immunogenic composition according to claim 2, wherein the adjuvant is selected from the group consisting of: recombinant particle of Hepatitis B Core Antigen, recombinant particle of Hepatitis C Core Antigen, OPC protein, KLH protein, Freund adjuvant, *Neisseria meningitides* p64k protein, and *Neisseria meningitides* outer membrane derived VSSP.

* * * * *

UNITED STATES PATENT AND TRADEMARK OFFICE
CERTIFICATE OF CORRECTION

PATENT NO. : 8,883,724 B2  
APPLICATION NO. : 12/612455  
DATED : November 11, 2014  
INVENTOR(S) : Romero et al.

Page 1 of 2

It is certified that error appears in the above-identified patent and that said Letters Patent is hereby corrected as shown below:

IN THE SPECIFICATION:

Column 1, line 50

Now reads: "growth factor P1GF"

Should read: -- growth factor PlGF --

Column 2, line 37

Now reads: "P1GF, described in 1991,"

Should read: -- PlGF, described in 1991, --

Column 2, line 40

Now reads: "With P1GF up-regulation"

Should read: -- With PlGF up-regulation --

Column 2, line 44

Now reads: "P1GF expression has"

Should read: -- PlGF expression has --

Signed and Sealed this  
Eighth Day of September, 2015

Michelle K. Lee  
*Director of the United States Patent and Trademark Office*

CERTIFICATE OF CORRECTION (continued)
U.S. Pat. No. 8,883,724 B2

Column 3, line 20

Now reads: "include VEGF-A, P1GF"

Should read: -- include VEGF-A, PlGF --

Column 4, line 18

Now reads: "and P1GF, increasing their"

Should read: -- and PlGF, increasing their --

Column 22, line 12

Now reads: "plasmid was digested Bg1II/"

Should read: -- plasmid was digested BgIII/ --